United States Patent
Hess et al.

(10) Patent No.: US 7,608,418 B2
(45) Date of Patent: Oct. 27, 2009

(54) NT-PROANP AND NT-PROBNP FOR DIAGNOSING CARDIAC DISEASES

(75) Inventors: Georg Hess, Mainz (DE); Andrea Horsch, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 70 days.

(21) Appl. No.: 11/945,309

(22) Filed: Nov. 27, 2007

(65) Prior Publication Data

US 2009/0042228 A1 Feb. 12, 2009

Related U.S. Application Data

(63) Continuation of application No. PCT/EP2006/062957, filed on Jun. 7, 2006.

(30) Foreign Application Priority Data

Jun. 7, 2005 (EP) .................................. 05012196

(51) Int. Cl.
*C12Q 1/02* (2006.01)
(52) U.S. Cl. ........................................................ 435/29
(58) Field of Classification Search ................... 435/17, 435/29
See application file for complete search history.

(56) References Cited

U.S. PATENT DOCUMENTS

| | | | |
|---|---|---|---|
| 2007/0141634 A1* | 6/2007 | Vuolteenaho et al. | 435/7.2 |
| 2007/0248981 A1* | 10/2007 | Snider et al. | 435/6 |
| 2008/0070315 A1* | 3/2008 | Hess et al. | 436/86 |
| 2008/0171354 A1* | 7/2008 | Hess et al. | 435/29 |
| 2008/0213746 A1* | 9/2008 | Ng et al. | 435/4 |
| 2008/0221033 A1* | 9/2008 | Seher et al. | 514/12 |
| 2009/0023591 A1* | 1/2009 | Spanuth | 506/7 |
| 2009/0081702 A1* | 3/2009 | Hess et al. | 435/7.4 |
| 2009/0081719 A1* | 3/2009 | Hess et al. | 435/29 |

OTHER PUBLICATIONS

Squire I. et al. N-Terminal pro-ANP . . . Clinical Science 107, 309-316, 2004.*
Daggubati S. et al. Adrenomedullin, Endothelin . . . Cardiovascular Research 36, 246-255, 1997.*
Jarai R., et al. Risk Assessment in Patients with Unstable Angina . . . European Heart Journal 26, 250-256, 2005.*
Richards, A., et al. Antecedent Hypertension and Heart Failure After Myocardial Infarction. J of the Americal College of Cardiology 39(7)1182-1188, 2002.*

* cited by examiner

*Primary Examiner*—Ralph Gitomer
(74) *Attorney, Agent, or Firm*—Marilyn Amick; Roche Diagnostics Operations, Inc.

(57) ABSTRACT

Described are methods for diagnosing a cardiac disease, particularly an acute cardiac event, in a patient presenting with symptoms of acute cardiac decompensation, comprising the steps of (a) measuring, typically in vitro, the level of NT-proBNP (N-terminal brain natriuretic peptide) or a variant thereof in a sample from the patient, (b) measuring, typically in vitro, the level of NIT-proANP (N-terminal atrial natriuretic peptide) or a variant thereof in a sample from the patient, (c) combining the information of the measured levels of NT-proANP and NT-proBNP, wherein an increased level of NT-proANP in presence of a non-increased or weakly increased level of NT-proBNP indicates the presence of an acute cardiac event, or wherein an increased level of NT-proANP in presence of a highly increased level of NT-proBNP indicates the presence of a chronic cardiac disease. The methods also allow distinguishing an acute cardiac event from decompensation of a chronic cardiac disease. Described also are corresponding kits and to methods of treatment of cardiac diseases.

10 Claims, No Drawings

NT-PROANP AND NT-PROBNP FOR DIAGNOSING CARDIAC DISEASES

This application is a continuation of PCT/EP2006/062957 filed Jun. 7, 2006 and claims priority to EP 05012196.1 filed Jun. 7, 2005.

The present invention relates to the use of biomarkers for diagnosis of cardiac diseases, in particular acute cardiac events and chronic cardiac diseases.

Cardiac diseases belong to the most common causes of morbidity and mortality in the northern hemisphere. Patients with cardiac diseases usually present to their general practitioner or to a hospital emergency room once they show symptoms of cardiac insufficiency, or even cardiac decompensation.

Cardiac decompensation usually requires a rapid and adequate therapeutic response. Particularly, in acute cardiac events such as myocardial infarction prognosis is best if treatment such as revascularization is performed as soon as possible. However, current diagnostic tools such as electrocardiography and echocardiography are, though widely used, insufficient to provide reliable diagnosis of cardiac disease. Therefore, cardiac disease is frequently misdiagnosed by general practitioners (Svendstrup Nielsen, L., et al. (2003). N-terminal pro-brain natriuretic peptide for discriminating between cardiac and non-cardiac dyspnca. The European Jounal of Heart Failure).

Furthermore, cardiac decompensation may be caused by different types of diseases. For example, acute cardiac decompensation may be caused by acute cardiac events but also by a decompensation of a chronic cardiac disease. To choose the best mode of treatment, it is advantageous to rapidly obtain information about the cause of a cardiac decompensation. However, the clinical symptoms of acute cardiac events can be very similar to those of an acute cardiac decompensation due to an underlying chronic cardiac disease.

Therefore, simple, fast, and reliable diagnostic tools are needed, in particular for general practitioners and/or physicians.

The use of biomarkers for diagnostic purposes is known as such. Atrial natriuretic peptide (ANP) and brain natriuretic peptide (BNP) are two members of the family of natriuretic or cardiac hormones. In vivo, ANP and BNP are generated by proteolytic cleavage of precursor molecules, resulting in the active hormone (ANP or BNP) and an N-terminal fragment (NT-proANP and NT-proBNP, respectively).

Natriuretic hormone assays have been discussed as prognostic markers in cardiovascular disease, in the follow-up of heart failure and as possibly reducing the need for further cardiac investigation (Clerico, A., Emdin, M. (2004). Diagnostic Accuracy and Prognostic Relevance of the Measurement of Cardiac Natriuretic Peptides: A Review. Clinical Chemistry 50:1, 33-50).

However, the relative diagnostic value of the different molecules ANP, BNP, NT-proANP and NT-proBNP is still under debate. According to a recent review, "although comparative, data are limited, N-ANP, BNP and N-BNP seem to provide qualitatively similar information". Therefore, "it remains to be established whether, in the diagnosis of heart failure, the simultaneous measurement of ANP and BNP (or N-ANP and N-BNP) can add value over that provided by ANP or BNP (N-ANP or N-BNP) alone. Because BNP is activated after more prolonged cardiac overload, ANP would be a good marker of acute volume load hemodynamic changes, and heart failure due to rapid release of stored atrial ANP" (Ruskoaho, H. (2003). Cardiac Hormones as Diagnostic Tools in Heart Failure. Endocrine Reviews 24(3): 341-356).

It has been stated that it is conceivable that ANP is a better marker of acute overload and/or rapid cardiovascular hemodynamic changes than BNP, or, especially, than NT-proANP or NT-proBNP (Clerico, A., Emdin, M. (2004), cited above). A very recent review states that BNP and NT-proBNP are more useful (concerning diagnosis) than the A-type natriuretic peptides (McMurry, J. J. V. and Pfeffer, M. A. (2005). Heart failure. Lancet, vol. 365:1877-89, see page 1879).

The picture is further complicated by the quite different molecular properties of the different natriuretic peptides. For example, ANP is a highly unstable molecule (having a half-life in plasma of 2-5 minutes). Special training and high diligence of the responsible personnel is required to obtain reliable results. Therefore, measurement of ANP appears not to be useful for regular clinical practice.

One actual study showed that BNP and ANP were both increased in patients suffering from acute myocardial infarction at the time of admission (Morita, E., Yasue, H., Yoshimura, M., et al. (1993). Increased plasma levels of brain natriuretic peptide in patients with acute myocardial infarction. Circulation, vol. 88(1): 82-91.

However, the study related only to the plasma levels of ANP and BNP in selected patients suffering from acute myocardial infarction, but not to a clinically realistic heterogeneous group of patients. In particular, the analyzed patients were selected based on an already increased level of CK-MB, which is a marker for necrosis. A necrosis marker indicates that a myocardial infarction has already caused severe and usually irreversible damage.

Thus, in the state of the art there is currently no biomarker which allows an early diagnosis of acute cardiac events and/or a distinction between acute and chronic cardiac insufficiency, typically before necrosis becomes evident.

Therefore, it is an object of the present invention to provide methods and means for improved early diagnosis of cardiac diseases, particularly for diagnosis of acute cardiac events. Another object of the present invention is to provide methods and means for distinguishing acute cardiac events from chronic cardiac diseases.

In a first embodiment, the object is achieved by a method for diagnosing a cardiac disease in a patient presenting with symptoms of acute cardiac decompensation, comprising the steps of measuring, typically in vitro, the level of NT-proANP or a variant thereof in a sample from the subject, measuring, typically in vitro, the level of NT-proBNP or a variant thereof in a sample from the subject, combining the information of the measured levels of NT-proANP and NT-proBNP, wherein an increased level of NT-proANP in presence of a non-increased or weakly increased level of NT-proBNP indicates the presence of an acute cardiac event, and/or wherein an increased level of NT-proANP in presence of a highly increased level of NT-proBNP indicates the presence of a chronic cardiac disease.

The present method also allows distinguishing an acute cardiac event from a chronic cardiac disease, particularly from decompensation of a chronic cardiac disease, in a patient presenting with symptoms of acute cardiac decompensation.

Analogously, the present invention also relates to a use of the combined information of the measured levels of NT-proANP and NT-proBNP for diagnosing, typically early diagnosing, a cardiac disease, particularly an acute cardiac event and/or a chronic cardiac disease, in a patient presenting with symptoms of acute cardiac decompensation. Such use may be adapted analogously to all other features and embodiments disclosed in the present specification and examples.

The method may also comprise the step of taking a sample, e.g., a body fluid or tissue sample, from the patient. Within the present invention, the taking of the body fluid or tissue sample can typically be carried out by non-medical staff (i.e. not having an education necessary for carrying out the profession of a physician). This applies in particular if the sample is blood.

In the context of the present invention, it has been found that NT-proANP and NT-proBNP show different time-courses of their plasma levels in the early phase of acute cardiac decompensation. These time-courses depend on the type of the underlying cardiac disease present in the patient. If the patient is suffering from chronic cardiac disease, the time-courses of the levels of NT-proANP and NT-proBNP are qualitatively similar. If the patient is suffering from an acute cardiac event, then NT-proBNP increases more slowly and the total level is lower than in chronic cardiac disease. In contrast, NT-proANP increases more rapidly than NT-proBNP and then decreases to a lower level than in chronic cardiac disease (see Example 1).

The present invention also provides improved safety in diagnosis of patients suffering from cardiac diseases. As laid out above, it has been found in the context of the present invention that NT-proBNP increases only with a considerable time lag after an acute cardiac event. Therefore, measurement of NT-proBNP briefly after an acute cardiac event may result in a false negative diagnosis or an underestimating of the extent of the cardiac dysfunction and may delay the initiation of cardiac treatment (see also Example 1). However, delayed cardiac treatment may severely affect the prognosis of a patient with cardiac insufficiency. On the other hand, it has been found in the context of the present invention that measurement of NT-proANP alone may lead to underestimating of the extent of the cardiac insufficiency or disease, as the level of NT-proANP may decrease within few hours after having reached a peak level.

Therefore, combined measurement of NT-proANP and NT-proBNP may help to avoid false or delayed diagnosis, particularly in an emergency setting.

As shown in Example 3, the method according the present invention is unlikely to indicate the presence of an acute cardiac event if merely ischemia and not a severe impairment of cardiac function is present.

The invention takes advantage of certain "biomarkers" (or simply "markers"), more particularly biochemical or molecular markers. The terms "biomarker", "biochemical marker" and "molecular marker" are known to the person skilled in the art. In particular, biochemical or molecular markers are gene expression products which are differentially expressed (i.e. upregulated or downregulated) in presence or absence of a certain condition, disease, or complication. Usually, a molecular marker is defined as a nucleic acid (such as an mRNA), whereas a biochemical marker is a protein or peptide. The level of a suitable biomarker can indicate the presence or absence of the condition or disease and thus allow diagnosis.

The present invention particularly takes advantage of NT-proANP and NT-proBNP as biomarkers, particularly as biochemical markers.

NT-proANP and NT-proBNP belong to the group of natriuretic peptides (see e.g., Bonow, R. O. (1996). New insights into the cardiac natriuretic peptides. Circulation 93: 1946-1950). As already mentioned, NT-proANP and NT-proBNP are generated by proteolytic cleavage from precursor molecules, the pre-pro peptides, resulting in the active hormones (ANP or BNP) and the corresponding N-terminal fragments (NT-proANP and NT-proBNP, respectively).

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

The different cleavage products show several different properties. BNP is produced predominantly (albeit not exclusively) in the ventricles and is released upon increase of wall tension. In contrast, ANP is produced and released exclusively from the atria. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NT-proBNP is 120 min longer than that of BNP, which is 20 min (Smith M W, Espiner E A, Yandle T G, Charles C J, Richards A M. Delayed metabolism of human brain natriuretic peptide reflects resistance to neutral endopeptidase. J Endocrinol. 2000; 167: 239-46.).

Preanalytics are robust with NT-proBNP, which allows easy transportation of the sample to a central laboratory (Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller T, Gegenhuber A, et al., Clin Chem Lab Med 2004; 42: 942-4, supra; Wu A H, Packer M, Smith A, Bijou R, Fink D, Mair J, Wallentin L, Johnston N, Feldcamp C S, Haverstick D M, Ahnadi C E, Grant A, Despres N, Bluestein B, Ghani F. Analytical and clinical evaluation of the Bayer ADVIA Centaur automated B-type natriuretic peptide assay in patients with heart failure: a multisite study. Clin Chem 2004; 50: 867-73.).

Similarly, preanalytics of NT-proANP are more robust than those of ANP. ANP is unstable in plasma or serum. ANP shows a plasma half-life of approximately 2 to 5 minutes as compared to approximately 40 to 50 minutes for NT-proANP.

Thus, the present invention provides robust biomarkers useful for daily clinical practice.

The term "variants" of NT-proANP or NT-proBNP relates to peptides substantially similar to NT-proANP or NT-proBNP. The term "substantially similar" is well understood by the person skilled in the art. In particular, a variant may be an isoform or allele which shows amino acid exchanges compared to the amino acid sequence of the most prevalent peptide isoform in the human population. Typically, such a substantially similar peptide has a sequence similarity to the most prevalent isoform of the peptide of at least 80%, typically at least 85%, more typically at least 90%, most typically at least 95%. Substantially similar are also degradation products, e.g., proteolytic degradation products, which are still recognized by the diagnostic means or by ligands directed against the respective full-length peptide.

The term "variant" also relates to a post-translationally modified peptide such as glycosylated peptide. A "variant" is also a peptide which has been modified after collection of the sample, for example by covalent or non-covalent attachment of a label, particularly a radioactive or fluorescent label, to the peptide. Measuring the level of a peptide modified after collection of the sample is understood as measuring the level of the originally non-modified peptide.

Examples of particular variants of NT-proANP and NT-proBNP and methods for their measurement are known (Ala-Kopsala, M., Magga, J., Peuhkurinen, K. et al. (2004): Molecular heterogeneity has a major impact on the measurement of circulating N-terminal fragments of A-type and B-type natriuretic peptides. Clinical Chemistry, vol. 50(9), 1576-1588).

The term "diagnosing" is known to the person skilled in the art. Diagnosing is understood as becoming aware of any medical condition, particularly a cardiac disease. Diagnosing also relates to "differential diagnosis", i.e. to distinguishing between different conditions with the same or similar symptoms. Particularly, differential diagnosis includes distinguishing an acute cardiac event from a chronic cardiac disease. In that case, the same or similar symptoms may be those of an acute cardiac decompensation.

Typically, the diagnostic information gained by the means and methods according to the present invention is interpreted by a trained physician. Typically, any decision about further treatment in an individual subject is also made by a trained physician. If deemed appropriate, the physician will also decide about further diagnostic measures.

The term "patient" according to the present invention typically relates to an individual suffering from a disease. The patient may have no known history of cardiovascular disease. Typically, the term "patient" relates to an individual showing symptoms of cardiac insufficiency, more particularly symptoms of acute cardiac decompensation. The symptoms of cardiac insufficiency or decompensation may be caused by a cardiac disease or an acute cardiac event.

The present invention broadly concerns the diagnosis of cardiac diseases. The term "cardiac disease" is known to the person skilled in the art. It relates to any kind of heart dysfunction, more particularly to heart dysfunctions affecting the pumping capability, more particularly it relates to "acute cardiac events" and "chronic cardiac diseases".

Patients suffering from a cardiac disease may be individuals suffering from stable angina pectoris (SAP) and individuals with acute coronary syndromes (ACS). ACS patients can show unstable angina pectoris (UAP) or these individuals have already suffered from a myocardial infarction (MI). MI can be an ST-elevated MI or a non-ST-elevated MI. The occurring of an MI can be followed by a left ventricular dysfunction (LVD). Finally, LVD patients undergo congestive heart failure (CHF) with a mortality rate of roughly 15%. Cardiac diseases according to the present invention also include coronary heart disease, heart valves defects (e.g., mitral valve defects), dilatative cardiomyopathy, hypertroph cardiomyopathy, and heart rhythm defects (arrythmias).

The person skilled in the art is familiar with the meaning of the terms "acute" and "chronic". The terms have opposite meanings, i.e. "acute" typically relates to a suddenly appearing condition or a temporarily severe condition or a condition which rapidly develops to a crisis, whereas "chronic" typically relates to a slowly developing condition or a slowly progressing condition, or a deep-seated or long-continued condition. However, a chronic condition may also develop into an acute condition after an extended period of stability or slow progression. The causes of acute or chronic conditions may be different or they may be similar and only different in their extent or severity.

In the context of the present invention, "acute cardiac events" are distinguished from "chronic cardiac diseases". These terms are familiar to the person skilled in the art. Typically, an "acute cardiac event" relates to an acute condition, disease or malfunction of the heart, particularly acute heart failure, e.g., myocardial infarction or arrhythmia. Depending on the extent of an MI, it may be followed by LVD and CHF.

Typically, a "chronic cardiac disease" is a weakening of heart function, e.g., due to ischemia of the heart, coronary artery disease, or previous, particularly small, myocardial infarction(s) (possibly followed by progressing LVD). It may also be a weakening due to inflammatory diseases, heart valve defects (e.g., mitral valve defects), dilatative cardiomyopathy, hypertroph cardiomyopathy, heart rhythm defects (arrhythmias), and chronic obstructive pulmonary disease (COPD, which is a disease affecting the airway of the lung, reducing the number of pulmonary alveoles, and secondarily affecting the heart). Thus, it is clear that a chronic cardiac disease may also include patients who had suffered from an acute coronary syndrome, e.g., MI, but who are presently not suffering from an acute cardiac event.

Symptomatically, cardiac diseases may result in "cardiac insufficiency". The term "cardiac insufficiency" is familiar to the person skilled in the art. Typically, cardiac insufficiency relates to the inability of the heart to circulate the blood sufficiently, particularly under conditions of increased need of oxygenation, such as during physical exercise. Cardiac insufficiency included both the instability to eject blood sufficiently (forward-failure) as well as the inability to sufficiently take up the venous backflow of blood to the heart (backward-failure).

Cardiac insufficiency may be classified according to a functional classification system established for cardiovascular diseases according to the New York Heart Association (NYHA). Patients of Class I have no obvious symptoms of cardiovascular disease. Physical activity is not limited, and ordinary physical activity does not cause undue fatigue, palpitation, or dyspnea (shortness of breath). Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased.

Another indicator of cardiac insufficiency is the "left ventricular ejection fraction" (LVEF) which is also known as "ejection fraction". People with a healthy heart usually have an unimpaired LVEF, which is generally described as above 50%. Most people with a systolic cardiac dysfunction which is symptomatic have an LVEF of 40% or less.

The term "cardiac decompensation" is familiar to the person skilled in the art. "Cardiac decompensation" generally refers to the most severe levels of cardiac insufficiency. During cardiac decompensation, the inability of the heart to circulate the blood sufficiently reaches a level at which the body's stress reactions are unable to compensate for the lack of pumping capacity. Symptoms of cardiac decompensation are known to the person skilled in the art. Particularly, a patient showing symptoms of "cardiac decompensation" is showing symptoms according to NYHA class II, III, IV, or worse. More particularly, the patient shows symptoms according to NYHA class III, IV or worse. Even more particularly, the patient shows symptoms according to NYHA class IV or worse. Most particularly, the patient requires clinical support to stabilize or maintain circulation.

The term "combining the information" of measured levels is readily understood by the person skilled in the art. Once the levels of two or more biomarkes according to the present invention have been measured, the information of the measured levels is evaluated. Combining means that the information of the biomarkers is typically not evaluated independently of each other but that the information is assembled into a single, typically diagnostic, information. As already laid out earlier, it has been found in the context of the present invention that a combined evaluation of the levels of NT-proANP and NT-proBNP, can provide more information than each marker alone or even than the sum of the markers. E.g., an increased level of NT-proANP in presence of a non-increased or weakly increased level of NT-proBNP indicates the presence of a cardiac disease, particularly of an acute cardiac event. Combining the information may also be performed by mathematical or boolean operations on the measured levels, e.g., by calculating a ratio between the measured levels. Typically, also the absolute levels are taken into consideration in such mathematical operation. Thus, combining the information typically relates to evaluating the measured levels of more than one biomarker. The term "evaluating" is known to the person skilled in the art. Typically, evaluating is understood as judging, appraising, or interpreting the measured level(s), more typically as judging, appraising or interpreting what the particular measured level(s) indicate.

The terms "non-increased", "increased", "weakly increased", or "highly increased" level refer to the level of a biomarker measured in a patient as compared to a known level indicative of the absence of a cardiac disease, particularly of the absence of an acute cardiac event or chronic cardiac disease.

The person skilled in the art is able to determine known level(s) (or, e.g., ratio(s)), see also Example 1. For example, a known level may be determined as the median or the average of the measured levels in a population of individuals not suffering from a cardiac disease. Evaluating the levels in further individuals or patients, e.g. in cohort studies, can help to refine the known levels or ratios. Analogously, it is also possible to define and/or refine reference levels indicative of the presence of an acute cardiac event or a chronic cardiac disease (see e.g., Example 1).

The known level may also be a "reference value". The person skilled in the art is familiar with the concept of reference values (or "normal values") for biomarkers. In particular, the term reference value may relate to the actual value of the level in one or more control samples or it may relate to a value derived from the actual level in one or more control samples. Typically, samples of at least 2, more typically at least 5, more typically at least 50, more typically at least 100, most typically at least 500 subjects are analyzed to determine the reference value.

In the most simple case, the reference value is the same as the level measured in the control sample or the average of the levels measured in a multitude of control samples. However, the reference value may also be calculated from more than one control sample. E.g., the reference value may be the arithmetic average of the level in control samples representing the control status (e.g., healthy, particular condition, or particular disease state). Typically, the reference value relates to a range of values that can be found in a plurality of comparable control samples (control samples representing the same or similar disease status), e.g., the average ± one or more times the standard deviation. Similarly, the reference value may also be calculated by other statistical parameters or methods, for example as a defined percentile of the level found in a plurality of control samples, e.g., a 90%, 95%, 97.5%, or 99% percentile. The choice of a particular reference value may be determined according to the desired sensitivity, specificity or statistical significance (in general, the higher the sensitivity, the lower the specificity and vice versa). Calculation may be carried out according to statistical methods known and deemed appropriate by the person skilled in the art.

The terms "control" or "control sample" are known to the person skilled in the art. Typically, the "control" relates to an experiment or test carried out to provide a standard, against which experimental results (e.g., the measured level(s) in a patient) can be evaluated. In the present context, the standard typically relates to the level of the biomarker of interest associated with a particular health or disease status. Thus, a "control" is typically a sample taken to provide such a standard. E.g., the control sample may be derived from one or more healthy subjects, or from one or more patients representative of a particular disease status. In the context of the present invention, patients representative of a particular disease status particularly include patients suffering from an acute cardiac event or a chronic cardiac disease, more particularly in presence of symptoms of acute cardiac decompensation. The control sample may also have been derived from the same subject or patient at an earlier time.

Examples for known levels or ratios are given further below. It will be possible to further refine such levels or ratios. The particular known levels or ratios given in this specification may serve as a guideline for diagnosis. As known and well-accepted in the art, actual diagnosis in the individual subject is typically carried out through individual analysis by a physician, e.g., depending on weight, age, general health status and anamnesis of the individual subject.

As already mentioned, the underlying cause of acute cardiac decompensation may be an acute event or an acute decompensation of a previously chronic cardiac disease. However, a patient suffering from a chronic cardiac disease may additionally suffer from an acute event, e.g., a patient whose heart function has already been impaired by previous infarctions or ischemia may suddenly suffer from a further myocardial infarction. It should be noted that in patients who are suffering from a chronic cardiac disease even a small acute cardiac event (such as a small myocardial infarction) may lead to acute cardiac decompensation.

Therefore, the method according to the present invention may typically deal with three groups of patients showing symptoms of acute cardiac decompensation: Patients suffering from acute cardiac events (1), patients suffering from chronic cardiac diseases who, presently suffer from an additional acute cardiac event (2), and patients suffering from a chronic cardiac disease which is acutely decompensating (3).

In the context of the present invention it was found that patients presenting with symptoms of acute decompensation caused by an acute cardiac event (above-mentioned patient group 1) show a non-increased or only weakly increased level of NT-proBNP but a highly increased level of NT-proANP at the time of admission to a hospital. Furthermore, in these patients the level of NT-proANP drops off rapidly within the first 12 hours after admission.

Furthermore, in the context of the present invention it was found that patients presenting with symptoms of acute decompensation who suffer from a chronic disease but are presently suffering from an additional acute cardiac event (above-mentioned patient group 2) show a non-increased or only weakly increased level of NT-proBNP but a highly increased level of NT-proANP at the time of admission to a hospital. Furthermore, in these patients the level of NT-proANP drops off rapidly within the first 12 hours after admission. This pattern is quite similar to the pattern observed in the patients who are not suffering from a chronic cardiac disease (patient group 1).

Furthermore, in the context of the present invention it was found that patients presenting with symptoms of acute decompensation caused by a chronic cardiac disease (above-mentioned patient group 3) show highly increased values of NT-proBNP and NT-proANP already at the time of admission to a hospital. The time-course of the levels of both biomarkers runs approximately parallel for the first 24 hours. Notably, the value of NT-proBNP is already highly increased at the time of admission. Furthermore, in the case of a chronic cardiac disease the levels of NT-proANP and NT-proBNP do not change as much over the first day after admission as in the case of an acute cardiac event (see also the Examples).

According to the findings in the context of the present invention the measured level of NT-proANP can depend on the severity of the cardiac disease: The more severe the cardiac disease, the higher the level of NT-proANP. Furthermore, the end of the acute event can be associated with a decrease of NT-proANP. In contrast, NT-proBNP reflects (mainly) the chronic cardiac disease and shows only slow changes. The measured levels may not only indicate presence or absence of a cardiac disease (particularly an acute cardiac event or a chronic cardiac disease) but also extent or severity of the disease. The measured levels therefore reflect the clinical continuum between patients suffering from a minor or a more severe cardiac disease. E.g., a very high level of NT-proANP indicates the presence of a more severe acute cardiac event.

The levels of NT-proANP and NT-proBNP in patients suffering from a chronic disease but presently suffering from an additional acute cardiac event (above-mentioned patient group 2) are similar to the levels in patient group 1 (acute cardiac event, but no chronic disease). Thus, the present invention appears to allow a diagnosis of an acute cardiac event independently of whether the patient has previously suffered from a chronic cardiac disease or not.

Notably, the present invention has been shown to provide clinically relevant data even according to a subjective time scale, i.e. time zero being the time of admission to a hospital, and not necessarily an objective time scale such as time lapsed since the onset of symptoms. The present scenario corresponds closely to the real-world clinical situation in which a first measurement is carried out at the time of admission and not according to a certain time lapsed since the onset of symptoms. This time can be quite variable, usually patients showing symptoms of acute cardiac decompensation present to a physician, particularly a hospital, within 30 minutes to 24 hours after the onset of symptoms.

According to the present invention, the term "non-increased level of NT-proBNP" typically corresponds to a plasma level of NT-proBNP of less than 125 pg/ml, particularly of less than 76 pg/ml, more particularly of less than 50 pg/ml.

According to the present invention, the term "weakly increased level of NT-proBNP" typically corresponds to a plasma level of NT-proBNP of 125 to 1000 pg/ml, particularly 125 to 900 pg/ml, more particularly 125 to 750 pg/ml.

According to the present invention, the term "highly increased level of NT-proBNP" typically corresponds to a plasma level of NT-proBNP of more than 3000 pg/ml.

According to the present invention, the term "increased level of NT-proANP" typically corresponds to a plasma level of NT-proANP of more than 3000 pg/ml, more particularly of more than 4000 pg 1 ml, even more particularly of more than, 7000 pg/ml, and most particularly of more than 10000 pg/ml.

Further typical level(s) can be derived from the upper limits of the reference intervals as described in Example 2.

It is evident that the combined information from NT-proANP and NT-proBNP may also be expressed differently. E.g., the relationship between NT-proANP and NT-proBNP may also be expressed as a "ratio". In general, the higher the measured ratio of NT-proANP to NT-proBNP in a sample of a patient showing symptoms of acute cardiac decompensation is, the more likely is it that the patient is suffering from an acute cardiac event (and belongs to above mentioned patient group 1 or 2). Particularly, a ratio of more than 35, more particularly a ratio of more than 50, most particularly a ratio of more than 70, indicates the presence of an acute cardiac event.

The mentioned levels of NT-proANP and NT-proBNP are considered to provide a first guidance to the person skilled in the art. It is within the abilities of the person skilled in the art to further refine the levels according to further data gained in clinical practice of clinical studies. For example, the levels can be further refined according to weight, age, and sex of the patients. For example, older apparently healthy subjects will typically show higher levels of NT-proANP or NT-proBNP than younger apparently healthy subjects (see also Example 2). Methods for defining suitable levels, including the statistical analysis of the data, are well known in the state of the art. Obviously, the person skilled in the art will have no difficulty in calculating moralities corresponding to the above defined levels expressed in pg/ml (see also Example 2)

Furthermore, the person skilled in the art is able to define corresponding levels for samples other than blood plasma.

As can be seen from the examples, measuring the level(s) of NT-proANP and/or NT-proBNP at at least one additional time-point may provide additional diagnostic information. For example, measurement of NT-proBNP may help to avoid underestimating the extent of a cardiac disease as compared to measuring NT-proANP alone after 12 hours or more since admission. Therefore, in one embodiment, the level of NT-proANP and/or NT-proBNP is measured in at least one additional sample, typically the sample being taken within a short time interval after first measurement. A suitable time may be, for example, within 2 to 12 hours, typically 4 to 12 hours after taking of the first sample.

Sampling and measuring may be carried out even more often, in order to establish a time-course of the level(s) of NT-proANP and/or NT-proBNP. Such time course may provide additional diagnostic information. For example, measurement of NT-proBNP may help to monitor the progression of the disease or the influence of treatment. Therefore, the present invention also relates to measuring the time-course of NT-proANP and NT-proBNP. Typically, the time-course is determined according to short intervals, e.g., the samples are taken every 12 hours, typically every 6 hours, more typically every 4 hours, most typically every 2 hours. Measurement at short intervals is typically made during the days after onset of symptoms or after admission of the patient to the hospital, e.g., during the first 4, 3, or 2 days.

In another embodiment, additional diagnostic parameters of cardiac disease are measured, particularly chosen from the group consisting of (a) left ventricular ejection fraction (LVEF), (b) echocardiogram (c) anamnesis (medical history), in particular concerning angina pectoris, (d) electrocardiogram, (e) parameters of thyroid or kidney function, (f) blood pressure, in particular arterial hypertension, (g) thallium scintigram, angiography, (i) catheterization.

These additional diagnostic parameters may be determined before, after, or in parallel to measuring NT-proANP and NT-proBNP. The additional diagnostic parameters may either establish a suspicion of the presence of a cardiac disease or they may serve to further evaluate the diagnostic relevance of a particular level or ratio measured.

It should be noted that symptoms of cardiac insufficiency can be similar to symptoms of other diseases than cardiac diseases. E.g., dyspnea and fatigue may also result from lung emboly, anemia, adipositas, lack of physical exercise, or a combination of those. As already laid out earlier, the teaching of the present invention helps to avoid a false negative diagnosis concerning a cardiac disease. Furthermore, using automated systems, it is possible to measure NT-proANP and NT-proBNP in a time of less than one hour. E.g., using the Elecsys™ analyzer analysis time for NT-proBNP is approximately 18 minutes (Ruskoaho, H. (2003), cited above). Thus, the present invention may even provide an earlier reliable and valuable diagnostic information than standard diagnostic methods for cardiac diseases, e.g., electrocardiography, echocardiography or invasive methods such as coronary angiography or hemodynamic monitoring. After taking of a sample, e.g., a blood sample, NT-proANP and NT-proBNP can be analyzed while other diagnostic methods a carried out in parallel.

Thus, in another embodiment, the present invention relates to method for diagnosis of a cardiac disease in a patient presenting with symptoms of acute cardiac decompensation, wherein NT-proANP and NT-proBNP are measured at the time of first visit of a physician (particularly a cardiologist) or at the time of admission to a hospital after the onset of the symptoms. Time of admission typically means within 24 hours, more typically within 12 hours, even more typically within 30 minutes after onset of the symptoms.

The term "measuring at the time of admission" relates to taking the sample for measurement within 4 hours, typically within 2 hours, more typically within 1 hour after admission. Admission typically relates to the time of the first visit to a physician (typically cardiologist) or to the first admission to a hospital or clinic after onset of symptoms onset of symptoms. Typically, it relates to first admission to a hospital or clinic, most typically to admission to the emergency unit of said hospital or clinic. "After onset of symptoms" typically relates to onset of the symptoms of acute cardiac decompensation. The sample may also be taken briefly before admission, e.g., during emergency treatment on location or while the patient is being transported to a physician, clinic, or hospital.

Measurement of NT-proANP and NT-proBNP may be, carried out in parallel or successively (e.g., NT-proBNP may be measured before NT-proANP and vice versa). Typically, measurement is carried out in parallel. The term "parallel" in this context relates to using samples taken at the same time, typically taken less than 2 hours apart, more typically taken less than 1 hour apart. Most typically "parallel" in this context relates to using the same sample. Typically, also determining the amount or concentration of the peptides in the sample is carried out at the same time.

In another embodiment, additionally at least one biomarker of necrosis is measured. Biomarkers for necrosis, particularly of cardiac necrosis, are known to the person skilled in the art. Such markers indicate the presence of myocardial infarction. Examples for biomarkers of necrosis include troponin T, CK (creatine kinase), CK-MB (creatine kinase muscle-brain), and myoglobin. E.g., the present invention also relates to a method for diagnosing an a cardiac disease, particularly an acute cardiac event, in a patient presenting with symptoms of acute cardiac decompensation, comprising the steps of (a) measuring, typically in vitro, the level of NT-proANP or a variant thereof in a sample from the patient, (b) measuring, typically in vitro, the level of NT-proBNP or a variant thereof in a sample from the patient, (c) measuring, typically in vitro, the level of a biomarker of necrosis or a variant thereof in a sample from the patient, (d) combining the information of the measured levels of NT-proANP and NT-proBNP, wherein an increased level of NT-proANP in presence of a non-increased or weakly increased level of NT-proBNP and in presence of a non-increased or weakly increased level of a biomarker of necrosis indicates the presence of a cardiac disease, particularly an acute cardiac event. Advantageously, this embodiment allows early diagnosis of a cardiac disease, particularly an acute cardiac event, even if the measured level of a biomarker of necrosis is not (or is yet) increased.

It is evident that the aforementioned method may be adapted analogously to all other embodiments of the present invention. E.g., in another embodiment, the present invention also relates to a use, typically in vitro, of the combined information of the measured levels of NT-proANP, NT-proBNP, and a biomarker of necrosis, for diagnosing, typically early diagnosing, a cardiac disease (particularly an acute cardiac event and/or a chronic cardiac disease) in a patient presenting with symptoms of acute cardiac decompensation.

The level of a biochemical or molecular marker can be determined by measuring the concentration of the protein (peptide or polypeptide) or the corresponding the transcript. In this context, the term "measuring" relates typically to a quantitative or semi-quantitative determination of the level.

The level can be measured by measuring the amount or the concentration of the peptide or polypeptide. Typically, the level is determined as the concentration in a given sample. For the purpose of the inventions it may not be necessary to measure the absolute level. It may be sufficient to measure the relative level compared to the level in an appropriate control. Measurement can also be carried out by measuring derivatives or fragments specific of the peptide or polypeptide of interest, such as specific fragments contained in nucleic acid or protein digests.

Measurement of nucleic acids, particularly mRNA, can be performed according to any method known and considered appropriate by the person skilled in the art.

Examples for measurement of RNA include Northern hybridization, RNAse protection assays, in situ hybridization, and aptamers, e.g., Sephadex-binding RNA ligands (Srisawat, C., Goldstein I. J., and Engelke, D. R. (2001). Sephadex-binding RNA ligands: rapid affinity purification of RNA from complex RNA mixtures. Nucleic Acids Research, vol. 29, no. 2 e4).

Furthermore, RNA can be reversely transcribed to cDNA. Therefore methods for measurement of DNA can be employed for measurement of RNA as well, e.g., Southern hybridization, polymerase chain reaction (PCR), Ligase chain reaction (LCR) (see, e.g., Cao, W. (2004) Recent developments in ligase-mediated amplification and detection. Trends in Biotechnology, vol. 22 (1), p. 38-44), RT-PCR, real time RT-PCR, quantitative RT-PCR, and microarray hybridization (see e.g., Frey, B., Brehm, U., and Kübler, G., et al. (2002). Gene expression arrays: highly sensitive detection of expression patterns with improved tools for target amplification. Biochemica, vol. 2 p. 27-29).

Measurement of DNA and RNA may also be performed in solution, e.g., using molecular beacons, peptide nucleic acids (PNA), or locked nucleic acids (LNA) (see e.g., Demidov, V. V. (2003). PNA and LNA throw light on DNA. Trends in Biotechnology, vol. 21(1), p. 4-6).

Measurement of proteins or protein fragments can be carried out according to any method known for measurement of peptides or polypeptides of interest. The person skilled in the art is able to choose an appropriate method.

The person skilled in the art is familiar with different methods of measuring the level of a peptide or polypeptide. The term "level" relates to amount or concentration of a peptide or polypeptide in the sample.

Measuring can be done directly or indirectly. Indirect measuring includes measuring of cellular responses, bound ligands, labels, or enzymatic reaction products.

Measuring can be done according to any method known in the art, such as cellular assays, enzymatic assays, or assays based on binding of ligands. Typical methods are described in the following.

In one embodiment, the method for measuring the level of a peptide or polypeptide of interest comprises the steps of (a) contacting the peptide or polypeptide with a suitable substrate for an adequate period of time, (b) measuring the amount of product.

In another embodiment, the method for measuring the level of a peptide or polypeptide of interest comprises the steps of (a) contacting the peptide or polypeptide with a specifically binding ligand, (b) (optionally) removing non-bound ligand, (c) measuring the amount of bound ligand.

In another embodiment, the method for measuring the level of a peptide or polypeptide of interest comprises the steps of (a) (optionally) fragmenting the peptides or polypeptides of a sample, (b) (optionally) separating the peptides or polypeptides or fragments thereof according to one or more biochemical or biophysical properties (e.g., according to binding to a solid surface or their run-time in a chromatographic setup), (c) determining the amount of one or more of the peptides, polypeptides, or fragments, (d) determining the identity of one or more of the peptides, polypeptides or fragments of step (c) by mass spectrometry. An overview of mass spectrometric methods is given e.g., by Richard D. Smith (2002). Trends in mass spectrometry instrumentation for proteomics. Trends in Biotechnology, Vol. 20, No. 12 (Suppl.), pp. S3-S7).

Other typical methods for measurement include measuring the amount of a ligand binding specifically to the peptide or polypeptide of interest. Binding according to the present invention includes both covalent and non-covalent binding.

A ligand according to the present invention can be any peptide, polypeptide, nucleic acid, or other substance binding to the peptide or polypeptide of interest. It is well known that peptides or polypeptides, if obtained or purified from the human or animal body, can be modified, e.g., by glycosylation. A suitable ligand according to the present invention may bind the peptide or polypeptide also via such sites.

Typically, the ligand should bind specifically to the peptide or polypeptide to be measured. "Specific binding" according to the present invention means that the ligand should not bind substantially to ("cross-react" with) another peptide, polypeptide or substance present in the sample investigated. Typically, the specifically bound protein or isoform should be bound with at least 3 times higher, more typically at least 10 times higher and even more typically at least 50 times higher affinity than any other relevant peptide or polypeptide.

Non-specific binding may be tolerable, particularly if the investigated peptide or polypeptide can still be distinguished and measured unequivocally, e.g., by separation according to its size (e.g., by electrophoresis), or by its relatively higher abundance in the sample.

Binding of the ligand can be measured by any method known in the art. Typically, the method is semi-quantitative or quantitative. Suitable methods are, described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). For measurement of enzymatic reaction products, typically the amount of substrate is saturating. The substrate may also be labeled with a detectable label prior to the reaction. Typically, the sample is contacted with the substrate for an adequate period of time. An adequate period of time refers to the time necessary for an detectable, typically measurable amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.)

The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is typically at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels ("e.g., magnetic beads", including paramagnetic and superparamagnetic labels), and fluorescent labels.

Enzymatically active labels include e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g., using a light-sensitive film or a suitable camera system). As for measuring the enzymatic reaction, the criteria given above apply analogously.

Typical fluorescent labels include fluorescent proteins (such as GFP and its derivatives), Cy3, Cy5, Texas Red, Fluorescein, and the Alexa dyes (e.g., Alexa 5689). Further fluorescent labels are available e.g., from Molecular Probes (Oregon). Also the use of quantum dots as fluorescent labels is contemplated.

Typical radioactive labels include 35S, 125I, 32P, 33P and the like. A radioactive label can be detected by any method known and appropriate, e.g., a light-sensitive film or a phosphor imager.

Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, solid phase immune tests, and mass spectrometry such as SELDI-TOF, MALDI-TOF, or capillary electrophoresis-mass spectrometry (CE-MS). Further methods known in the art (such as gel electrophoresis, 2D gel electrophoresis, SDS polyacrylamid gel electrophoresis (SDS-PAGE), Western Blotting), can be used alone or in combination with labeling or other detection methods as described above.

Furthermore, suitable methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Typical ligands include antibodies, nucleic acids, peptides or polypeptides, and aptamers, e.g., nucleic acid or peptide aptamers. Methods to such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display.

The term "antibody" as used herein includes both polyclonal and monoclonal antibodies, as well as fragments thereof, such as Fv, Fab and F(ab)2 fragments that are capable of binding antigen or hapten.

In another embodiment, the ligand, typically chosen from the group consisting of nucleic acids, peptides, polypeptides, more typically from the group consisting of nucleic acids, antibodies, or aptamers, is present on an array.

Said array contains at least one additional ligand, which may be directed against a peptide, polypeptide or a nucleic acid of interest. Said additional ligand may also be directed against a peptide, polypeptide or a nucleic acid of no particular interest in the context of the present invention. Typically, ligands for at least three, typically at least five, more typically at least eight peptides or polypeptides of interest in the context of the present invention are contained on the array.

Binding of the ligand on the array may be detected by any known readout or detection method, e.g., methods involving optical (e.g., fluorescent), electrochemical, or magnetic signals, or surface plasmon resonance.

According to the present invention, the term "array" refers to a solid-phase or gel-like carrier upon which at least two compounds are attached or bound in one-, two- or three-dimensional arrangement. Such arrays (including "gene chips", "protein chips", antibody arrays and the like) are generally known to the person skilled in the art and typically generated on glass microscope slides, specially coated glass slides such as polycation-, nitrocellulose- or biotin-coated slides, cover slips, and membranes such as, for example, membranes based on nitrocellulose or nylon. The array may include a bound ligand or at least two cells expressing each at least one ligand.

It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g., a microbead or microsphere, is present in suspension. The array consists of different microbeads or microspheres, possibly labeled, carrying different ligands.

The invention further relates to a method of producing arrays as defined above, wherein at least one ligand is bound to the carrier material in addition to other ligands.

Methods of producing such arrays, for example based on solid-phase chemistry and photo-labile protective groups, are generally known (U.S. Pat. No. 5,744,305). Such arrays can also be brought into contact with substances or substance libraries and tested for interaction, for example for binding or change of confirmation. Therefore, arrays comprising a peptide or polypeptide as defined above may be used for identifying ligands binding specifically to said peptides or polypeptides.

Peptides and polypeptides (proteins) can be measured in tissue, cell, and body fluid samples, i.e. typically in vitro. Typically, the peptide or polypeptide of interest is measured in a body fluid sample.

A tissue sample according to the present invention refers to any kind of tissue obtained from the dead or alive human or animal body. Tissue samples can be obtained by any method known to the person skilled in the art, for example by biopsy or curettage.

Body fluids according to the present invention may include blood, blood serum, blood plasma, lymphe, cerebral liquor, saliva, vitreous humor, and urine. Particularly, body fluids include blood, blood serum, blood plasma, and urine. Samples of body fluids can be obtained by any method known in the art.

Some of the samples, such as urine samples, may only contain degradation products, in particular fragments, of the peptide or polypeptide of interest. However, as laid out above, measurement of the level may still be possible as long as the fragments are specific for the peptide or polypeptide of interest.

If necessary, the samples may be further processed before measurement. For example, nucleic acids, peptides or polypeptides may be purified from the sample according to methods known in the art, including filtration, centrifugation, or extraction methods such as chloroform/phenol extraction.

Furthermore, it is contemplated to use so called point-of-care or lab-on-a-chip devices for obtaining the sample and measuring the peptide or polypeptide of interest. Such devices may be designed analogously to the devices used in blood glucose measurement. Thus, a patient will be able to obtain the sample and measure the peptide or polypeptide of interest without immediate assistance of a trained physician or nurse.

In another embodiment, the present invention relates to a kit comprising (a) a means or device for measuring the level of NT-proANP in a sample from a patient, and (b) a means or device for measuring the level of NT-proBNP in a sample from a patient. Typically, the means according to (a) is a ligand binding specifically to NT-proANP, and/or the means according to (b) is a ligand binding specifically to NT-proBNP. Additionally, the kit may comprise a means or device, particularly a specifically binding ligand, for measuring the level of a biomarker of necrosis in a sample from a patient.

In another embodiment, the present invention relates to the use of such a kit for in vitro diagnosis of an acute cardiac event, particularly for distinguishing an acute cardiac event from a chronic cardiac disease, in a patient presenting with symptoms of acute cardiac decompensation.

In another embodiment, the present invention relates to the use of a ligand specifically binding NT-proANP and/or a ligand specifically binding to NT-proBNP for the manufacture of a diagnostic kit for diagnosis, particularly for early diagnosis, of a cardiac disease (e.g., an acute cardiac event or a chronic cardiac disease), particularly for distinguishing an acute cardiac event form a chronic cardiac disease, in a patient presenting with symptoms of acute cardiac decompensation. Additionally, a ligand specifically binding to a biomarker of necrosis, may be used for manufacture of such a kit.

The present invention also relates to methods of treatment of cardiac diseases. Once a patient has been diagnosed, it may have consequences for the subsequent treatment. If a method according to the present invention indicates that a cardiac disease is present in the patient then treatment may be initiated or adapted. The level(s) and/or ratio(s) of NT-proANP and NT-proBNP in subject may be monitored at regular intervals. Also during such a period of monitoring, the present invention allows to detect a cardiac disease, particularly an acute cardiac event. Furthermore, the subject may be investigated intensively by further diagnosis according to methods known to the skilled cardiologist, such as described earlier in this specification, e.g., electrocardiography, or echocardiography. Treatment may include any measures which generally are associated with improving or restoring heart function. E.g., treatment with non-steroidal anti-inflammatory drugs (e.g., Cox-2 inhibitors or selective Cox-2 inhibitors such as celecoxib or rofecoxib) may be discontinued or the dosage of any such drugs administered may be reduced. Other possible measures are restriction of salt intake, regular moderate exercise, providing influenzal and pneumococcal immunization, surgical treatment (e.g., revascularization, ballon dilatation, stenting, by-pass surgery), administering drugs such as diuretics (including co-administration of more than one diuretic), ACE (angiotensin converting enzyme) inhibitors, β-adrenergic blockers, aldosteron antagonists, calcium antagonists (e.g., calcium channel blockers), angiotensin-receptor blockers, digitalis, as well as any other measures known and deemed appropriate; by the person skilled in the art.

Treatment of an acute cardiac event may be different from treatment of a chronic cardiac disease. If a method according to the present invention indicates the presence of an acute cardiac event, then treatment may focus on administration of loop diuretics (such as furosemide, turosemide, or ethacrynic acid), catecholamines, and early revasularization.

If a method according to the present invention indicates the presence of a chronic disease but no additional acute cardiac event, then treatment may rather focus on assisting circulation, e.g., heart-lung machine or balloon catheterization.

Further treatment options available to the person skilled in the art are described in McMurray, J. J. V. and Pfeffer, M. A. (2005). Heart failure. Lancet vol. 365, pp. 1877-89, see particularly pp. 1879-1885)

More particularly, in a further embodiment, the present invention relates to a method for deciding on the possible treatment of a patient for a cardiac disease, wherein the patient presents with symptoms of acute cardiac decompensation, comprising the steps of (a) measuring, typically in vitro, the level of NT-proANP or a variant thereof in a sample from the patient, (b) measuring, typically in vitro, the level of NT-proBNP or a variant thereof in a sample from the patient, (c) combining the information of the measured levels of NT-proANP and NT-proBNP, wherein an increased level of NT-proANP in presence of a non-increased or weakly increased level of NT-proBNP indicates the presence of an acute cardiac event, or wherein an increased level of NT-proANP in presence of a highly increased level of NT-proBNP indicates the presence of a chronic cardiac disease, (d) optionally initiating an examination of the patient by a cardiologist, (e) recommending the initiation of the treatment or refraining from the treatment, optionally in consideration of the result of the patient's examination by the cardiologist.

Typically, initiating an examination by a cardiologist and/or initiating treatment is recommended if the method indicates the presence of a cardiac disease. The method relates to all diseases and condition mentioned earlier in this specification, particularly to initiating treatment of an acute cardiac event or a chronic cardiac disease. Typically, the treatment of an acute cardiac event or an chronic cardiac disease is initiated or recommended if the evaluation in step (c) indicates the presence of either event or disease. It is evident that the method may be adapted according to all embodiments or aspects of the invention mentioned in this specification.

EXAMPLE 1

The study population of this trial was composed of patients with acutely decompensated heart failure of ischemic and non-ischemic origin within the previous 24 hours. Diagnosis of decompensated heart failure and cardiogenic shock, derived from the guidelines of the European Society of Cardiologists as described below, was assessed by cardiologists blinded for plasma levels of biomarkers. All patients had evidence of heart failure from ischemic or non-ischemic origin. All patients received diuretics or antianginous therapy before randomization. The essential end point of the present study was mortality within the first 30 days of follow-up. The local ethics committee approved the study, and written informed consent was obtained from all participating subjects or relatives.

Biochemical Analysis

In the 114 patients enrolled in this trial, plasma samples for the determination of the cardiac markers were collected at baseline (n=117), 12 hours (n=105), 24 hours (n=103) and 48 hours (n=102). NT-proBNP was measured with a chemiluminescent immunoassay kit (Roche Diagnostics) on an Elecsys 2010 analyzer (measuring range, 5 to 35 000 pg/mL; the intra-assay coefficient of variation is 0.9% at mean values of 474 pg/mL, 1.1% at mean values of 8005 pg/mL, and 0.9% at mean values of 13 682 pg/mL). All samples were stored at −80° C. before analysis, and biomarker measurements were performed in samples that underwent only a single thaw cycle.

Biochemical analysis was performed as follows: After thawing, the plasma was analyzed for the NT-proANP by a competitive binding radioimmunoassay with magnetic solid phase technique, in a modification of Sundsfjord et al.

(Sundsfjord, J. A., Thibault, G., Larochelle, P., and Cantin, M. (1988). Identification and plasma concentration of the N-terminal fragment of proatrial natriuretic factor in man. J. Clin Endocrinol Metab 1988, vol. 66, pp. 605-610), by using the same anti-rat proANP polyclonal serum, human proANP (1-30) from Peninsula Laboratories (Bachem, St. Helene, UK) as the standard, and iodined proANP (1-30) purified by HPLC for radiolabeling. To achieve high sensitivity and good precision, Dynabeads M280 with sheep anti-rabbit IgG (Dynal Biotech, Oslo, Norway) as solid-phase and second antibody were used. The interassay coefficient of variation was ≦7.5%.

Results

The following tables 2 to 5 show the data belonging to a subset of the patients as described above.

TABLE 2

Levels of NT-proANP, NT-proBNP, and troponin T observed in patients suffering from acute cardiac events. Data are shown for samples obtained at the time of admission as well as for samples obtained at ½ day and 1 day after admission.

| Patient number | Adm. | ½ day | 1 day | Diagnosis |
|---|---|---|---|---|
| patient 093 | | | | |
| NT-proBNP (pg/ml) | 103 | 327 | 341 | Acute |
| NT-proANP (pg/ml) | 14,995 | 5,813 | 5,259 | cardiogenic |
| Troponin T (µg/L) | 0.01 | 0.01 | 0.01 | shock |
| patient 086 | | | | |
| NT-proBNP (pg/ml) | 229 | 2,572 | 2,231 | Acute |
| NT-proANP (pg/ml) | 17,821 | 6,847 | 8,099 | myocardial |
| Troponin T (µg/L) | 0.29 | 3.13 | 2.88 | infarction |
| patient 025 | | | | |
| NT-proBNP (pg/ml) | 679 | 4,032 | 3,513 | Acute |
| NT-proANP (pg/ml) | 58,529 | 19,665 | 13,028 | myocardial |
| Troponin T (µg/L) | 0.23 | 1.51 | 0.73 | injury |
| patient 019 | | | | |
| NT-proBNP (pg/ml) | <5 | 1,923 | 4,654 | Acute |
| NT-proANP (pg/ml) | 23,353 | 11,650 | 7,569 | myocardial |
| Troponin T (µg/L) | 0.01 | 17.59 | 9.84 | infarction |

TABLE 2-continued

Levels of NT-proANP, NT-proBNP, and troponin T observed in patients suffering from acute cardiac events. Data are shown for samples obtained at the time of admission as well as for samples obtained at ½ day and 1 day after admission.

| Patient number | Adm. | ½ day | 1 day | Diagnosis |
|---|---|---|---|---|
| patient 005 | | | | |
| NT-proBNP (pg/ml) | 76 | 754 | 1,583 | Acute |
| NT-proANP (pg/ml) | 25,071 | 6,735 | 5,655 | myocardial |
| Troponin T (µg/L) | 0.09 | 22.71 | 12.06 | infarction |

Abbreviations:
Adm., time of admission;
n, not determined

Further data of the patients:

| patient no. | age (years) | gender (m/f) | died (y/n) |
|---|---|---|---|
| 093 | 38 | m | n |
| 086 | 63 | m | n |
| 025 | 66 | m | y |
| 019 | 63 | m | y |
| 005 | 45 | m | n |

Note that patients No. 005 and 019 showed NT-proBNP values which were either perfectly normal (patient 019) or below a cut-off of 125 pg/ml. Also the troponin T levels in both patients were normal at the time of admission. These values would indicate that both patients were not suffering from cardiac disease. In truth, both patients were suffering from severe acute cardiac events, in the case of patient 019 even leading to death. However, both patients showed an increased level of NT-proANP at the time of admission which, according to the teaching of the present invention, would have indicated the presence of an acute cardiac event.

TABLE 2a

Levels of NT-proANP, NT-proBNP, and troponin T observed in further patients suffering from acute cardiac events. Data are shown for samples obtained at the time of admission as well as for samples obtained at ½ day and 1 day after admission.

| | Adm. | ½ day | 1 day | diagnosis |
|---|---|---|---|---|
| patient 013 | | | | |
| NT-proBNP (pg/ml) | 49 | 2193 | 2887 | acute myocardial infarction |
| NT-proANP (pg/ml) | 12901 | 5258 | 4137 | |
| Troponin T (µg/L) | 0.01 | 8.12 | 9.34 | |
| patient 014 | | | | |
| NT-proBNP (pg/ml) | n | 1299 | 1845 | acute myocardial infarction |
| NT-proANP (pg/ml) | n | 2002 | 1252 | |
| Troponin T (µg/L) | n | 18.82 | 8.14 | |
| patient 015 | | | | |
| NT-proBNP (pg/ml) | 0 | 2026 | n | acute myocardial infarction |
| NT-proANP (pg/ml) | 5854 | 3194 | 2889 | |
| Troponin T (µg/L) | 0.02 | 3.13 | n | |

TABLE 2a-continued

Levels of NT-proANP, NT-proBNP, and troponin T observed in further patients suffering from acute cardiac events. Data are shown for samples obtained at the time of admission as well as for samples obtained at ½ day and 1 day after admission.

|  | Adm. | ½ day | 1 day | diagnosis |
|---|---|---|---|---|
| patient 023 | | | | |
| NT-proBNP (pg/ml) | <5 | <5 | <5 | penicillin allergy |
| NT-proANP (pg/ml) | 2177 | 2181 | 1956 | |
| Troponin T (µg/L) | 0.2 | 0.23 | 0.17 | |
| patient 40 | | | | |
| NT-proBNP (pg/ml) | 339 | 9421 | 10965 | acute arhythmia, cerebral tumor, sepsis! |
| NT-proANP (pg/ml) | 13111 | 7642 | 7572 | |
| Troponin T (µg/L) | 0.23 | 0.26 | 0.18 | |
| patient 052 | | | | |
| NT-proBNP (pg/ml) | 11.1 | 527.8 | 533.4 | acute myocardial infarction |
| NT-proANP (pg/ml) | 5819 | 932 | 915 | |
| Troponin T (µg/L) | 0.07 | 3.81 | 2.74 | |
| patient 053 | | | | |
| NT-proBNP (pg/ml) | 220.7 | 826.9 | 634.3 | acute myocardial infarction |
| NT-proANP (pg/ml) | 9360 | 1360 | 1052 | |
| Troponin T (µg/L) | 12.92 | 10.24 | 7.45 | |
| patient 078 | | | | |
| NT-proBNP (pg/ml) | 39 | 37.5 | 35.1 | exclusion coronary artery disease |
| NT-proANP (pg/ml) | 1560 | 1374 | 1266 | (acute event, but not necessarily of cardiac origin) |
| Troponin T (µg/L) | 0.01 | 0.01 | 0.01 | |
| patient 092 | | | | |
| NT-proBNP (pg/ml) | 485.8 | | 5600.2 | acute myocardial injury |
| NT-proANP (pg/ml) | 5013 | n | 2401 | |
| Troponin T (µg/L) | 2.45 | | 6.16 | |
| patient 111 | | | | |
| NT-proBNP (pg/ml) | 175.5 | 269.8 | 282.6 | acute cardiac event, MI |
| NT-proANP (pg/ml) | 2647 | 1325 | 1339 | |
| Troponin T (µg/L) | 0.63 | 2.15 | 1.05 | |
| patient 125 | | | | |
| NT-proBNP (pg/ml) | 51.5 | 423.4 | 245.6 | ventricular fibrillation of unknown origin |
| NT-proANP (pg/ml) | 4031 | 1136 | 1420 | (acute event) |
| Troponin T (µg/L) | 0.27 | 0.03 | 0.01 | |
| patient 127 | | | | |
| NT-proBNP (pg/ml) | 70.6 | 81 | 98.9 | hypertensive crisis (acute event, |
| NT-proANP (pg/ml) | 2314 | 2517 | 2356 | not necessarily with cardiac event) |
| Troponin T (µg/L) | 0.01 | 0.01 | 0.01 | |

Abbreviations:
Adm., time of admission;
n, not determined

TABLE 3

Levels of NT-proANP, NT-proBNP, and troponin T observed in patients suffering from chronic cardiac disease but presently suffering from an additional acute cardiac event.

|  | Adm. | ½ day | 1 day | diagnosis |
|---|---|---|---|---|
| patient 114 | | | | |
| NT-proBNP (pg/ml) | 723 | 1180 | 790 | previous myocardial infarction |
| NT-proANP (pg/ml) | 32,448 | 8,751 | 8,050 | acute asystolic event |
| Troponin T (µg/L) | 0.49 | 0.5 | 0.55 | |
| patient 051 | | | | |
| NT-proBNP (pg/ml) | 525 | 1,676 | 1,289 | Coronary artery disease |
| NT-proANP (pg/ml) | 19,665 | 9,463 | 8,506 | Acute myocardial infarction |
| Troponin T (µg/L) | 2.44 | 2.6 | 2.1 | |

TABLE 3-continued

Levels of NT-proANP, NT-proBNP, and troponin T observed in patients suffering from chronic cardiac disease but presently suffering from an additional acute cardiac event.

|  | Adm. | ½ day | 1 day | diagnosis |
|---|---|---|---|---|
| patient 050 | | | | |
| NT-proBNP (pg/ml) | 425 | 2,837 | 3,051 | Coronary artery disease |
| NT-proANP (pg/ml) | 69,075 | 27,901 | 15,731 | Acute myocardial infarction |
| Troponin T (µg/L) | 18.82 | 32.7 | 23.75 | |

Further data of the patients:

| patient No. | age (years) | gender (m/f) | died (y/n) |
|---|---|---|---|
| 114 | 64 | m | n |
| 051 | 51 | m | n |
| 050 | 62 | m | n |

TABLE 3a

Levels of NT-proANP, NT-proBNP, and troponin T observed in further patients suffering from chronic cardiac disease but presently suffering from an additional acute cardiac event

|  | Adm. | ½ day | 1 day | diagnosis |
|---|---|---|---|---|
| patient 042 | | | | |
| NT-proBNP (pg/ml) | 4817.9 | 16358.5 | | COPD, cardiomyopathy, acute event. (MI) |
| NT-proANP (pg/ml) | 13286 | 10166 | n | |
| Troponin T (µg/L) | 2.86 | 2.28 | | |
| patient 047 | | | | |
| NT-proBNP (pg/ml) | 825.94 | 2735.2 | 5498.47 | chronic heart failure, acute MI |
| NT-proANP (pg/ml) | 5539 | 6065 | 7572 | |
| Troponin T (µg/L) | 1.18 | 11.63 | 7.2 | |
| patient 054 | | | | |
| NT-proBNP (pg/ml) | 8405 | 17005 | 12653 | chronic heart failure, acute ischemia event |
| NT-proANP (pg/ml) | 19106 | 11604 | 12410 | |
| Troponin T (µg/L) | 1.11 | 6.54 | 5.95 | |
| patient 074 | | | | |
| NT-proBNP (pg/ml) | 2890.7 | 9546.2 | 15667.4 | chronic heart failure, acute MI |
| NT-proANP (pg/ml) | 24820 | 13917 | 8729 | |
| Troponin T (µg/L) | 13.41 | 13.89 | 8.82 | |
| patient 081 | | | | |
| NT-proBNP (pg/ml) | 8235.1 | 11613.6 | 8337.7 | chronic heart failure, acute MI |
| NT-proANP (pg/ml) | 17318 | 11919 | 10762 | |
| Troponin T (µg/L) | 18.62 | 20.48 | 15.24 | |
| patient 088 | | | | |
| NT-proBNP (pg/ml) | 4290.6 | 7054 | 7665.9 | chronic heart failure, acute ventricular arrhythmia |
| NT-proANP (pg/ml) | 36213 | 25381 | 24750 | |
| Troponin T (µg/L) | 0.01 | 0.03 | 0.01 | |
| patient 090 | | | | |
| NT-proBNP (pg/ml) | 2402.9 | 6143.1 | 3544.8 | chronic heart failure, acute arhythmia |
| NT-proANP (pg/ml) | 12094 | 4312 | 4698 | |
| Troponin T (µg/L) | 0.01 | 0.26 | 0.14 | |

TABLE 3a-continued

Levels of NT-proANP, NT-proBNP, and troponin T observed in further patients suffering from chronic cardiac disease but presently suffering from an additional acute cardiac event

|  | Adm. | ½ day | 1 day | diagnosis |
|---|---|---|---|---|
| patient 091 | | | | |
| NT-proBNP (pg/ml) | 745 | 1593.5 | 2779.3 | cardiogenic schock, acute arhythmia, |
| NT-proANP (pg/ml) | 12200 | 4908 | 2166 | chronic heart failure |
| Troponin T (µg/L) | 0.15 | 4.46 | 2.81 | |
| patient 113 | | | | |
| NT-proBNP (pg/ml) | 2027 | 3772 | 4600 | chronic heart failure, ventriculare, fibrillation, |
| NT-proANP (pg/ml) | 10482 | 8343 | 8098 | acute cardiac event |
| Troponin T (µg/L) | 0.01 | 0.01 | 0.01 | |
| patient 119 | | | | |
| NT-proBNP (pg/ml) | 1879 | 11910 | 12747 | chronic heart failure, acute cardiac event |
| NT-proANP (pg/ml) | 12585 | 5048 | 6626 | (Arhythmia?) |
| Troponin T (µg/L) | 0.47 | 0.92 | 0.85 | |
| patient 121 | | | | |
| NT-proBNP (pg/ml) | 2332 | 4350 | 4313 | chronic heart failure, acute MI |
| NT-proANP (pg/ml) | 5013 | 2703 | 3025 | |
| Troponin T (µg/L) | 5.76 | 9.16 | 3.59 | |
| patient 122 | | | | |
| NT-proBNP (pg/ml) | n | 1389 | 3599 | chronic heart failure, acute cardiac event (MI) |
| NT-proANP (pg/ml) | n | 5819 | 3576 | |
| Troponin T (µg/L) | n | 3.49 | 3.41 | |
| patient 126 | | | | |
| NT-proBNP (pg/ml) | 4928 | 5039 | 4026 | chronic heart failure, impaired kidney function, |
| NT-proANP (pg/mL) | 26362 | 14303 | 11148 | acute MI |
| Troponin T (µg/L) | 3.15 | 18.31 | 12.84 | |
| patient 128 | | | | |
| NT-proBNP (pg/ml) | 7645 | 25227 | 7133 | cardiomyopathy, chronic heart failure, |
| NT-proANP (pg/ml) | 34075 | 29728 | 15179 | cardiogenic schock, ventricular fibrillation |
| Troponin T (µg/L) | 0.04 | 0.01 | 0.01 | (chronic HF + acute event) |

TABLE 4

Levels of NT-proANP, NT-proBNP, and troponin T observed in patients suffering from chronic cardiac disease

|  | Adm. | ½ day | 1 day | diagnosis |
|---|---|---|---|---|
| patient 112 | | | | |
| NT-proBNP (pg/ml) | 560 | 1,087 | 1,759 | previous myocardial infarction, COPD, acute |
| NT-proANP (pg/ml) | 24,335 | 29,373 | 30,358 | decompensation |
| Troponin T (µg/L) | 0.21 | 0.06 | 0.01 | |
| patient 100 | | | | |
| NT-proBNP (pg/ml) | 4,771 | 7,014 | 6,545 | Previous myocardial infarction, absolute |
| NT-proANP (pg/ml) | 58,014 | 54,203 | 52,236 | arrhythmia, acute decompensation |
| Troponin T (µg/L) | | | 0.1 | |
| patient 087 | | | | |
| NT-proBNP (pg/ml) | 4,032 | 6,784 | 2,806 | Previous myocardial infarction, tachyarrhythmia, |
| NT-proANP (pg/ml) | 44,368 | 33,675 | 36,136 | absolute, acute decompensation |
| Troponin T (µg/L) | 0.01 | 0.01 | 0.01 | |
| patient 077 | | | | |
| NT-proBNP (pg/ml) | 309 | 947 | 763 | Acute myocardial infarction, cardiogenic shock |
| NT-proANP (pg/ml) | 10,213 | 6,774 | 5,259 | |
| Troponin T (µg/L) | 9.73 | 14.04 | 4.49 | |

TABLE 4-continued

Levels of NT-proANP, NT-proBNP, and troponin T observed in patients suffering from chronic cardiac disease

|  | Adm. | ½ day | 1 day | diagnosis |
|---|---|---|---|---|
| patient 072 | | | | |
| NT-proBNP (pg/ml) | 5,928 | 3,549 | 662 | Coronary artery disease, heart failure, acute decompensation |
| NT-proANP (pg/ml) | 50,514 | 17,207 | 19,297 | |
| Troponin T (µg/L) | 0.15 | 0.19 | 0.16 | |
| patient 066 | | | | |
| NT-proBNP (pg/ml) | 934 | 1,930 | 3,901 | Coronary artery disease, previous PCI, minor acute myocardial infarction |
| NT-proANP (pg/ml) | 29,868 | 26,425 | 21,755 | |
| Troponin T (µg/L) | 0.78 | 8.8 | 8.25 | |
| patient 058 | | | | |
| NT-proBNP (pg/ml) | 1,507 | 1,168 | 902 | Cardiomyopathy, atrial fibrillation, acute decompensation |
| NT-proANP (pg/ml) | 39,330 | 33,675 | 33,062 | |
| Troponin T (µg/L) | 0.01 | 0.01 | 0.01 | |
| patient 034 | | | | |
| NT-proBNP (pg/ml) | 318 | 603 | 504 | Coronary artery disease, minor acute myocardial infarction |
| NT-proANP (pg/ml) | 5,999 | 5,666 | 5,827 | |
| Troponin T (µg/L) | 1.49 | 1.64 | 1.1 | |
| patient 007 | | | | |
| NT-proBNP (pg/ml) | 1,220 | 436 | 265 | COPD, acute decompensation |
| NT-proANP (pg/ml) | 11,468 | 8,099 | 8,790 | |
| Troponin T (µg/L) | 0 | 0 | 0 | |
| | Aufnahme | | | |
| patient 003 | | | | |
| NT-proBNP (pg/ml) | 53,724 | 33,443 | 20,009 | Coronary artery disease, ventricular fibrillation, acute decompensation |
| NT-proANP (pg/ml) | 30,358 | 21,509 | 21,018 | |
| Troponin T (µg/L) | 22.8 | 9.7 | 7.8 | |

Abbreviations:
COPD, chronic obstructive pulmonary disease;
PCI, percutaneous coronary intervention Further data of the patients:

| patient No. | age (years) | gender (m/f) | died (y/n) |
|---|---|---|---|
| 112 | 77 | m | y |
| 100 | 62 | m | n |
| 087 | 73 | m | n |
| 077 | 35 | m | n |
| 066 | 84 | f | y |
| 058 | 51 | m | n |
| 034 | 54 | m | n |
| 007 | 72 | f | n |
| 003 | 69 | m | n |

TABLE 4a

Levels of NT-proANP, NT-proBNP, and troponin T observed in further patients suffering from chronic cardiac disease

|  | Adm. | ½ day | 1 day | diagnosis |
|---|---|---|---|---|
| patient 004 | | | | |
| NT-proBNP (pg/ml) | 79998 | 43135 | | chronic heart failure |
| NT-proANP (pg/ml) | 26923 | 21840 | n | |
| Troponin T (µg/L) | 0.02 | 0.02 | | |
| patient 009 | | | | |
| NT-proBNP (pg/ml) | 3830 | 2994 | 3080 | chronic heart failure |
| NT-proANP (pg/ml) | 4137 | 3425 | 3611 | |
| Troponin T (µg/L) | 0 | 0.03 | 0.03 | |

TABLE 4a-continued

Levels of NT-proANP, NT-proBNP, and troponin T observed in further patients suffering from chronic cardiac disease

|  | Adm. | ½ day | 1 day | diagnosis |
|---|---|---|---|---|
| patient 011 | | | | |
| NT-proBNP (pg/ml) | 5316 | 5256 | 4769 | chronic heart failure |
| NT-proANP (pg/ml) | 3716 | 3926 | 3996 | |
| Troponin T (µg/L) | 5.14 | 3.8 | 3.99 | |
| patient 017 | | | | |
| NT-proBNP (pg/ml) | 12334 | 11759 | | impaired kidney function, chronic heart failure |
| NT-proANP (pg/ml) | 37019 | 36669 | n | |
| Troponin T (µg/L) | 32.87 | 67.77 | | |
| patient 021 | | | | |
| NT-proBNP (pg/ml) | 6599 | 4774 | 1121 | COPD, chronic heart failure |
| NT-proANP (pg/ml) | 3576 | 4102 | 2997 | |
| Troponin T (µg/L) | 0.01 | 0.01 | 0 | |
| patient 026 | | | | |
| NT-proBNP (pg/ml) | 13089 | 12077 | 15240 | chronic heart failure, cardiogenic shock |
| NT-proANP (pg/ml) | 39053 | 47396 | 50060 | |
| Troponin T (µg/L) | 0.05 | 0.09 | 0.08 | |
| patient 027 | | | | |
| NT-proBNP (pg/ml) | 14932 | n | 15397 | chronic heart failure |
| NT-proANP (pg/ml) | 18089 | n | 17809 | |
| Troponin T (µg/L) | 0.02 | n | 0.01 | |
| patient 028 | | | | |
| NT-proBNP (pg/ml) | 24797 | n | 23509 | chronic heart failure |
| NT-proANP (pg/ml) | 26853 | n | 36213 | |
| Troponin T (µg/L) | 0.14 | n | 0.21 | |
| patient 030 | | | | |
| NT-proBNP (pg/ml) | 2959.8 | 2390.5 | 2174.7 | COPD, artrial fibrillation, chronic heart failure |
| NT-proANP (pg/ml) | 7050 | 7397 | 7730 | |
| Troponin T (µg/L) | 0.01 | 0.02 | 0.03 | |
| patient 031 | | | | |
| NT-proBNP (pg/ml) | 3027 | 2909.2 | 5516.9 | ventricular arrhythmia, chronic heart failure, |
| NT-proANP (pg/ml) | 30534 | 16441 | 9886 | lung cancer |
| Troponin T (µg/L) | 0.03 | 0.17 | 0.12 | |
| patient 032 | | | | |
| NT-proBNP (pg/ml) | 5025 | 2391.7 | 1199.9 | decompensated chronic heart failure, COPD |
| NT-proANP (pg/ml) | 7572 | 5960 | 6065 | |
| Troponin T (µg/L) | 0.04 | 0.07 | 0.1 | |
| patient 033 | | | | |
| NT-proBNP (pg/ml) | 1101 | 880.1 | 1013.8 | recovery from MI (not acute), |
| NT-proANP (pg/ml) | 1844 | 1700 | 2279 | coronary artery disease |
| Troponin T (µg/L) | 8.92 | 6.72 | 5.07 | |
| patient 035 | | | | |
| NT-proBNP (pg/ml) | 13585 | n | 12915 | chronic heart failure |
| NT-proANP (pg/ml) | 18650 | n | 14198 | |
| Troponin T (µg/L) | 0.01 | n | 0.01 | |
| patient 37 | | | | |
| NT-proBNP (pg/ml) | | 15594 | 15239 | chronic heart failure |
| NT-proANP (pg/ml) | 18299 | 15775 | 26713 | |
| Troponin T (µg/L) | | 2.18 | 2.54 | |
| patient 38 | | | | |
| NT-proBNP (pg/ml) | 5065.9 | n | 5351.6 | chronic heart failure |
| NT-proANP (pg/ml) | 7782 | 7642 | 7537 | |
| Troponin T (µg/L) | 0.01 | n | 0.01 | |

TABLE 4a-continued

Levels of NT-proANP, NT-proBNP, and troponin T observed in further patients suffering from chronic cardiac disease

| | Adm. | ½ day | 1 day | diagnosis |
|---|---|---|---|---|
| patient 039 | | | | |
| NT-proBNP (pg/ml) | 1258.8 | 4623.6 | 7957.9 | COPD, chronic heart failure, |
| NT-proANP (pg/ml) | 9045 | n | 7677 | coronary artery disease |
| Troponin T (µg/L) | 2.14 | 4.11 | 2.92 | |
| patient 041 | | | | |
| NT-proBNP (pg/ml) | 400.1 | 1395.8 | 428.5 | COPD, chronic heart failure |
| NT-proANP (pg/ml) | 2657 | 2391 | 1791 | |
| Troponin T (µg/L) | 0.01 | 0.01 | 0.01 | |
| patient 43 | | | | |
| NT-proBNP (pg/ml) | 22213 | 24996 | 24293 | cardiomyopathy, chronic heart failure |
| NT-proANP (pg/ml) | 51673 | 50586 | 45854 | |
| Troponin T (µg/L) | 0.29 | 0.36 | 0.4 | |
| patient 044 | | | | |
| NT-proBNP (pg/ml) | n | 3390 | 3061.5 | chronic heart failure, acute decompensation |
| NT-proANP (pg/ml) | n | 2100 | 2058 | |
| Troponin T (µg/L) | 0.04 | 0.81 | 0.42 | |
| patient 048 | | | | |
| NT-proBNP (pg/ml) | 5856.2 | n | 6064 | chronic heart failure |
| NT-proANP (pg/ml) | 13076 | n | 11639 | |
| Troponin T (µg/L) | 0.02 | n | 0.02 | |
| patient 049 | | | | |
| NT-proBNP (pg/ml) | 6033.6 | 7441.6 | 8957.6 | chronic heart failure |
| NT-proANP (pg/ml) | 7607 | 6976 | 6626 | |
| Troponin T (µg/L) | 0.1 | 0.1 | 0.1 | |
| patient 056 | | | | |
| NT-proBNP (pg/ml) | 4226.9 | 4576.6 | 3457.5 | chronic heart failure, valve disorder |
| NT-proANP (pg/ml) | 9185 | 10131 | 11148 | |
| Troponin T (µg/L) | 0.01 | 0.01 | 0.01 | |
| patient 057 | | | | |
| NT-proBNP (pg/ml) | 4164.6 | 4703.2 | 3799.6 | chronic heart failure |
| NT-proANP (pg/ml) | 18054 | 14023 | 13987 | |
| Troponin T (µg/L) | 0.11 | 0.1 | 0.09 | |
| patient 059 | | | | |
| NT-proBNP (pg/ml) | 11361 | 15777 | 13063 | cardiomyopathy, chronic heart failure |
| NT-proANP (pg/ml) | 21770 | 32497 | 27730 | |
| Troponin T (µg/L) | 0.01 | 0.05 | 0.02 | |
| patient 060 | | | | |
| NT-proBNP (pg/ml) | 3530 | 22008 | 13158 | chronic heart failure, impaired renal function, |
| NT-proANP (pg/ml) | 26608 | 19772 | 13882 | ventricular arhythmia |
| Troponin T (µg/L) | 0.68 | 0.56 | 0.29 | |
| patient 062 | | | | |
| NT-proBNP (pg/ml) | 13255 | 13327 | 6881 | chronic heart failure |
| NT-proANP (pg/ml) | 18895 | 7327 | 6661 | |
| Troponin T (µg/L) | 0.52 | 0.54 | 0.4 | |
| patient 063 | | | | |
| NT-proBNP (pg/ml) | 13246 | 13568 | 11335 | chronic heart failure |
| NT-proANP (pg/ml) | 16582 | 18124 | 17002 | |
| Troponin T (µg/L) | 0.01 | 0.01 | 0.01 | |
| patient 067 | | | | |
| NT-proBNP (pg/ml) | 18883.1 | 25135.6 | | chronic heart failure |
| NT-proANP (pg/ml) | 52584 | 51182 | n | |
| Troponin T (µg/L) | 0.95 | 1.59 | | |

TABLE 4a-continued

Levels of NT-proANP, NT-proBNP, and troponin T observed in further patients suffering from chronic cardiac disease

|  | Adm. | ½ day | 1 day | diagnosis |
|---|---|---|---|---|
| patient 068 | | | | |
| NT-proBNP (pg/ml) | 5690.4 | 4504.4 | 2537.6 | chronic heart failure, hyperthropic cardiomyopathy |
| NT-proANP (pg/ml) | 9886 | 9781 | 10131 | |
| Troponin T (μg/L) | 0.02 | 0.01 | 0.04 | |
| patient 069 | | | | |
| NT-proBNP (pg/ml) | 5952.6 | 6810.3 | 5231.2 | chronic heart failure |
| NT-proANP (pg/ml) | 10342 | 17072 | 13181 | |
| Troponin T (μg/L) | 0.01 | 0.01 | 0.01 | |
| patient 070 | | | | |
| NT-proBNP (pg/ml) | 8078.6 | 8160 | 6850.7 | chronic heart failure |
| NT-proANP (pg/ml) | 16652 | 15074 | 15740 | |
| Troponin T (μg/L) | 0.13 | 0.12 | 0.14 | |
| patient 071 | | | | |
| NT-proBNP (pg/ml) | 5112.9 | 5495.1 | 4187.5 | chronic heart failure |
| NT-proANP (pg/ml) | 12796 | 16126 | 15705 | |
| Troponin T (μg/L) | 0.01 | 0.01 | 0.01 | |
| patient 073 | | | | |
| NT-proBNP (pg/ml) | 22164.3 | 28183.7 | 21936.3 | chronic heart failure |
| NT-proANP (pg/ml) | 36669 | 35828 | 25836 | |
| Troponin T (μg/L) | 0.34 | 0.92 | 0.7 | |
| patient 076 | | | | |
| NT-proBNP (pg/ml) | 8959.4 | 28161.3 | 33622 | chronic heart failure, Brady/Tachy arhythmia |
| NT-proANP (pg/ml) | 26222 | 19772 | 17668 | |
| Troponin T (μg/L) | 0.87 | 0.72 | 0.39 | |
| patient 079 | | | | |
| NT-proBNP (pg/ml) | 3281.9 | 3963.7 | 3258.9 | cardiomyopathy, chronic heart failure |
| NT-proANP (pg/ml) | 20438 | 18720 | 15425 | |
| Troponin T (μg/L) | 0.25 | 0.24 | 0.25 | |
| patient 082 | | | | |
| NT-proBNP (pg/ml) | 42417.5 | 49797 | 74590 | chronic heart failure, impaired kidney function |
| NT-proANP (pg/ml) | 23908 | 34951 | 35582 | |
| Troponin T (μg/L) | 5.87 | 7.1 | 11.74 | |
| patient 083 | | | | |
| NT-proBNP (pg/ml) | 7076 | 6839.8 | 8934 | chronic heart failure, pulmonary hypertension |
| NT-proANP (pg/ml) | 11078 | 10973 | 12550 | |
| Troponin T (μg/L) | 0.01 | 0.01 | 0.01 | |
| patient 084 | | | | |
| NT-proBNP (pg/ml) | 14219.5 | 15636.4 | 26697 | cardiomyopathy, chronic heart failure |
| NT-proANP (pg/ml) | 36494 | 36459 | 36108 | |
| Troponin T (μg/L) | 0.03 | 0.04 | 0.05 | |
| patient 085 | | | | |
| NT-proBNP (pg/ml) | 8232.3 | 10445.3 | 7926.3 | cardiomyopathy, chronic heart failure, impaired kidney function |
| NT-proANP (pg/ml) | 31516 | 15004 | 12585 | |
| Troponin T (μg/L) | 0.13 | 0.15 | 0.12 | |
| patient 095 | | | | |
| NT-proBNP (pg/ml) | 5618.2 | 10578 | 10677.4 | chronic heart failure, acute decompensation |
| NT-proANP (pg/ml) | 15390 | 18825 | 15320 | |
| Troponin T (μg/L) | 0.01 | 0.06 | 0.32 | |
| patient 096 | | | | |
| NT-proBNP (pg/ml) | 11443.4 | 9180 | 7389.1 | chronic heart failure |
| NT-proANP (pg/ml) | 14093 | 13532 | 14794 | |
| Troponin T (μg/L) | 0.04 | 0.04 | 0.03 | |

TABLE 4a-continued

Levels of NT-proANP, NT-proBNP, and troponin T observed in further patients suffering from chronic cardiac disease

|  | Adm. | ½ day | 1 day | diagnosis |
|---|---|---|---|---|
| patient 098 | | | | |
| NT-proBNP (pg/ml) | 4967.8 | 5629.4 | 5538.4 | pulmonary hyperthension, chronic heart failure |
| NT-proANP (pg/ml) | 9535 | 9921 | 9045 | |
| Troponin T (µg/L) | 0.01 | 0.01 | 0.94 | |
| patient 099 | | | | |
| NT-proBNP (pg/ml) | 9999.9 | 6438.4 | 3653.7 | chronic heart failure |
| NT-proANP (pg/ml) | 7397 | 5469 | 5118 | |
| Troponin T (µg/L) | 1.11 | 1.06 | 1.96 | |
| patient 101 | | | | |
| NT-proBNP (pg/ml) | 2497.7 | 3937.3 | 3620.8 | chronic heart failure |
| NT-proANP (pg/ml) | 8238 | 6976 | 7572 | |
| Troponin T (µg/L) | 0.01 | 0.01 | 0.01 | |
| patient 103 | | | | |
| NT-proBNP (pg/ml) | 821 | 1545.8 | 6976.9 | chronic heart failure and chronic, |
| NT-proANP (pg/ml) | 14618 | 16512 | 15004 | cardiac necrosis |
| Troponin T (µg/L) | 4.65 | 7.21 | 5.49 | |
| patient 104 | | | | |
| NT-proBNP (pg/ml) | 14472.6 | 26252.8 | 35796 | decompensated dilatative, cardiomyopathy |
| NT-proANP (pg/ml) | 19281 | 15495 | 10692 | |
| Troponin T (µg/L) | 1.78 | 1.87 | 4.26 | |
| patient 105 | | | | |
| NT-proBNP (pg/ml) | 1111.3 | 5075.7 | | chronic heart failure, progressive necrosis |
| NT-proANP (pg/ml) | 28816 | 39403 | n | |
| Troponin T (µg/L) | 12.11 | 60.99 | | |
| patient 106 | | | | |
| NT-proBNP (pg/ml) | 2283.1 | 2179.3 | 2022.6 | chronic heart failure |
| NT-proANP (pg/ml) | 8133 | 9080 | 9045 | |
| Troponin T (µg/L) | 0.17 | 0.23 | 0.19 | |
| patient 107 | | | | |
| NT-proBNP (pg/ml) | 26790.6 | 38119 | 29291.8 | chronic heart failure |
| NT-proANP (pg/ml) | 16301 | 15425 | 10622 | |
| Troponin T (µg/L) | 0.68 | 1.18 | 1.79 | |
| patient 108 | | | | |
| NT-proBNP (pg/ml) | 12498.7 | 82240 | 65074.4 | chronic heart failure |
| NT-proANP (pg/ml) | 39824 | 37370 | 29482 | |
| Troponin T (µg/L) | 1.22 | 3.12 | 3 | |
| patient 109 | | | | |
| NT-proBNP (pg/ml) | 3075.9 | 423 | 717.1 | chronic heart failure |
| NT-proANP (pg/ml) | 7712 | 6766 | 7572 | |
| Troponin T (µg/L) | 0.01 | 0.01 | 0.01 | |
| patient 110 | | | | |
| NT-proBNP (pg/ml) | 22240.6 | 23300 | 20904.7 | chronic heart failure |
| NT-proANP (pg/ml) | 17107 | 16547 | 18510 | |
| Troponin T (µg/L) | 0.1 | 0.11 | 0.13 | |
| patient 115 | | | | |
| NT-proBNP (pg/ml) | 13211 | 26963 | 20739 | chronic heart failure, cardiomyopathy |
| NT-proANP (pg/ml) | 15039 | 12375 | 17388 | |
| Troponin T (µg/L) | 2.15 | 2.04 | 3.01 | |
| patient 117 | | | | |
| NT-proBNP (pg/ml) | 8475 | 11243 | 5395 | chronic heart failure |
| NT-proANP (pg/ml) | 16932 | 12200 | 9430 | |
| Troponin T (µg/L) | 0.11 | 0.8 | 0.94 | |
| patient 118 | | | | |
| NT-proBNP (pg/ml) | 2868 | 2233 | 1302 | chronic heart failure |
| NT-proANP (pg/ml) | 5609 | 7327 | 6030 | |
| Troponin T (µg/L) | 0.01 | 0.01 | 0.01 | |

TABLE 4a-continued

Levels of NT-proANP, NT-proBNP, and troponin T observed in further patients suffering from chronic cardiac disease

|  | Adm. | ½ day | 1 day | diagnosis |
|---|---|---|---|---|
| patient 120 | | | | |
| NT-proBNP (pg/ml) | 1806 | 8648 | 10158 | chronic heart failure, ventricular Tachy cardiac |
| NT-proANP (pg/ml) | 16827 | 13286 | 9080 | |
| Troponin T (μg/L) | 0.63 | 1.89 | 1.38 | |
| patient 123 | | | | |
| NT-proBNP (pg/ml) | 11239 | 6946 | 3380 | chronic heart failure |
| NT-proANP (pg/ml) | 10412 | 6766 | 4838 | |
| Troponin T (μg/L) | 0.05 | 0.1 | 0.08 | |

For better overview, the arithmetic averages of the levels measured in the patients according to Tables 2, 3, and 4 have been determined and are listed in the following Table 5.

TABLE 5

Arithmetic averages of the measured levels according to Tables 2, 3, and 4.

| | acute cardiac event | | | chronic cardiac disease plus acute cardiac event | | | chronic cardiac disease | | |
|---|---|---|---|---|---|---|---|---|---|
| | adm | 0.5 day | 1 day | adm | 0.5 day | 1 day | adm | 0.5 day | 1 day |
| NT-proBNP | 220 | 1900 | 2500 | 560 | 1900 | 1700 | 8100 | 6300 | 4200 |
| NT-proANP | 28000 | 10000 | 7900 | 40000 | 15000 | 11000 | 34000 | 26000 | 26000 |
| ratio of NT-proANP to NT-proBNP | 127 | 5.3 | 3.2 | 71 | 7.9 | 6.5 | 4.2 | 4.1 | 6.2 | adm: time of admission

EXAMPLE 2

NT-ProBNP with the RIA method: Competitive-binding radioimmunoassay with magnetic solid phase technique (modification of Sundsfjord et al. cited earlier).

Measuring range, undiluted: 60 to 10 000 pmol/L

Functional sensitivity: 100 pmol/L (equals 350 pg/ml)

1 pmol/L NT-proANP corresponds to 3.506 pg/ml NT-proANP

TABLE 6

Upper limit of the reference interval for NT-proANP

| Age of patient | upper limit of reference interval (pmol/L) | upper limit of reference interval (pg/ml) |
|---|---|---|
| <40 years | 800 | 2800 |
| 40-49 years | 900 | 3150 |
| 50-59 years | 1000 | 3500 |
| 60-69 years | 1200 | 4200 |
| 70-79 years | 1500 | 5260 |
| >80 years | 2000 | 7000 |

The values in Table 6 describe the upper limit of the NT-proANP values found in 97.5% of apparently healthy subjects. However, according to experience, this range may still include some patients suffering from cardiac diseases.

EXAMPLE 3

Patients suspected of having coronary heart disease were subjected to physical strain or artificial cardiac strain evoked by a drug (dipyridamole, which is a vasodilator). In patients with coronary heart disease, the strain will result in pain and/or changes in the electrocardiogram. In the present study, the patients were also analyzed by thallium scintigraphy. The thallium scintigram allows to recognize whether strain causes ischemia. The results were grouped as ischemia not being detectable, being persistent, or being reversible. A shown in Table 8, subjects without ischemia had significantly lower, NT-proBNP and NT-proANP levels.

TABLE 8

Levels (and ratios) of NT-proBNP and NT-proANP, and troponin T in patients subjected to cardiac strain as described above. The samples were taken before applying strain as well as 20 minutes and 4 hours after strain.

| Time sampling | no signs of ischemia (N = 61) | ischemia (total) (N = 78) | ischemia (persistent) (N = 54) | ischemia (reversible) (N = 24) |
|---|---|---|---|---|
| | Median NT-proANP, pg/ml | | | |
| before strain | 2566.392 | 4750.63 | 4610.39 | 5153.82 |
| 20 min | 2839.86 | 4698.04 | 4820.75 | 4943.46 |
| 4 hours | 2692.608 | 3926.72 | 4066.96 | 4715.57 |

TABLE 8-continued

Levels (and ratios) of NT-proBNP and NT-proANP, and troponin T in patients subjected to cardiac strain as described above. The samples were taken before applying strain as well as 20 minutes and 4 hours after strain.

| Time sampling | no signs of ischemia (N = 61) | ischemia (total) (N = 78) | ischemia (persistent) (N = 54) | ischemia (reversible) (N = 24) |
|---|---|---|---|---|
| Median NT-proBNP, pg/ml | | | | |
| before strain | 139 | 484 | 535 | 327 |
| 20 min | 161 | 442 | 586 | 311 |
| 4 hours | 169 | 462 | 547 | 318 |
| ratio of NT-proANP to NT-proBNP | | | | |
| before strain | 18.5 | 9.8 | 8.6 | 15.7 |
| 20 min | 17.6 | 10.6 | 8.2 | 15.9 |
| 4 hours | 15.9 | 8.5 | 7.4 | 14.8 |

Furthermore, the ratio of the levels of NT-proANP to NT-proBNP were significantly higher in patients without ischemia than in patients with ischemia.

Patients showing ischemia in the above test have an impairment of cardiac function due to an earlier cardiac damage. Patients showing no ischemia in the thallium scintigram have no significant arteriosclerosis and consequently usually no significantly impaired cardiac function.

Notably, the above date indicate that ischemia is insufficient to evoke a rapid and strong increase of NT-proANP and NT-proBNP comparable to the increase observed in patients showing symptoms of acute cardiac decompensation due to an acute cardiac event or chronic cardiac disease (e.g., in contrast to acute myocardial infarction and or a severe heart rhythm defect).

EXAMPLE 4

The following data show the time-courses of NT-proANP and NT-proBNP in patients with chronic heart failure and in patients with acute myocardial infarction. The data show that in patients with acute myocardial infarction there is a pronounced antidromic time-course of the values observed for NT-proBNP vs. NT-proANP.

TABLE 9

| | NT-proBNP (pg/ml) | | | NT-proANP (pg/ml) | | |
|---|---|---|---|---|---|---|
| | 0 | 12 h | 24 h | 0 | 12 h | 24 h |
| Chronic Heart Failure | | | | | | |
| Median | 5928 | 6946 | 6698 | 15845 | 13532 | 12024 |
| Change % | 100% | 117.2% | 113.0% | 100% | 85.4% | 75.9% |
| Delta % | | +17.2% | +13.0% | | −14.6% | −24.1% |
| Acute Myocardial Infarction | | | | | | |
| Median | 723 | 2383 | 3513 | 8589 | 5048 | 3025 |
| Change % | 100% | 330% | 486% | 100% | 59% | 35.2% |
| Delta % | | +230% | +386% | | −41% | −64.8% |

EXAMPLE 5

Acute coronary syndromes (ACS)

A total of 19 patients with acute coronary syndrome and a recent acute event were investigated and blood samples where taken at time zero (within 2 hours after begin of chest pain), 4 hours, and sometimes also later. The values of troponin T in all patients were initially negative. 12 of the patients showed measurable levels of troponin T at 4 hours (see, Table 11)

Due to their symptoms and shape of the ECG all patients underwent an angiography. In most patients a stent had to be implanted (see Table 11).

NT-proBNP was measured at time zero and after 3 to 4 hours (in some patients also at 1 and 2 hours). In a subgroup of the patients there was an increase of NT-proANP, both in the troponin T negative and the troponin T positive groups.

An increase of NT-proANP was associated with an increase of NT-proBNP. In contrast, if the level of NT-proANP decreased or remained unchanged, then the level of NT-proBNP remained unchanged or increased only slightly (see Table 10).

It can be concluded that in case of ACS there are pronounced changes of the levels of NT-proANP, whereas the changes of NT-proBNP are considerable less distinct. Furthermore, the levels of NT-proANP and NT-proBNP are largely independent from the level of troponin T. It is also visible, that not only troponin T positive patients were in need of therapeutic intervention, but also troponin T negative patients. The latter fact underlines the advantage of measuring NT-proANP and/or NT-proBNP, either independently or in addition to measuring the level of troponin T.

TABLE 10

| Patients N = 19 | Δ NT-proBNP [%] Mean NT-proBNP | Δ NT-proBNP [%] Mean NT-proBNP | Developed troponin (+) |
|---|---|---|---|
| Time Point | 0 (baseline) | 3 h | N |
| NT-proANP, Mean | 5607.1 pg/ml | 7035.8 pg/ml | |
| Increase > 20%; N = 9 (47%) | Δ 0% 169.3 pg/ml | Δ + 26% 212.7 pg/ml | 6/9 |
| Δ + 20%; N = 5 (26%) | Δ 0% 324.0 pg/ml | Δ + 10% 355.4 pg/ml | 3/5 |
| Decrease > 20%; N = 5 (26%) | Δ 0% 304.2 pg/ml | Δ + 1% 308.3 pg/ml | 3/5 |

During the clinical observation at the time of admission there were no sure signs of ECG changes or symptoms which would have unequivocally allowed a diagnosis of acute coronary syndrome. The final diagnosis was made later and is listed in the following table.

TABLE 11

Data of the 19 patients mentioned in the text, the first number in the sample no. indicates the number of the patient. In columns "lysis", "PCTA", "Stent", the numbers 0, 1, and 2 indicate, whether a thrombus had to be lysed, or a PTCA (percutaneous transluminal coronary angioplasty) had to be performed or a stent had to be inserted in the following, and how often this had been necessary.

| Sample No. | Time interval hours | TnT Class | TnT level ng/ml | hs-TnT pg/ml | NT-proBNP pg/ml | NT-proANP pg/ml | Diagnosis | Lysis | PTCA | Stent |
|---|---|---|---|---|---|---|---|---|---|---|
| 1__14:21 neg | 0 | Neg | | 1.8 | 30.9 | 4600 | NSTEMI | 0 | 1 | 1 |
| 1__18:26 pos | 4 | Pos | 0.06 | 20.3 | 23.0 | 6400 | NSTEMI | 0 | 1 | 1 |
| 2__13:57 neg | 0 | Neg | | 22.0 | 305.4 | 13800 | STEMI | 0 | 1 | 1 |
| 2__16:28 pos | 3 | Pos | 0.42 | 481.4 | 354.2 | 27400 | STEMI | 0 | 1 | 1 |
| 3__14:44 neg | 0 | Neg | | 11.6 | 247.0 | 10100 | STEMI | 0 | 1 | 1 |
| 3__17:52 pos | 3 | Pos | 0.28 | 230.7 | 340.7 | 12500 | STEMI | 0 | 1 | 1 |
| 4__09:54 neg | 0 | Neg | | 2.9 | 139.1 | 8000 | STEMI | 1 | 1 | 1 |
| 4__12:00 pos | 2 | Pos | 1.62 | 972.3 | 170.7 | 6100 | STEMI | 1 | 1 | 1 |
| 5__13:57 neg | 0 | Neg | | 27.9 | 288.4 | <635 | STEMI | 0 | 1 | 1 |
| 5__16:40 pos | 3 | Pos | 0.06 | 70.9 | 219.8 | <635 | STEMI | 0 | 1 | 1 |
| 6__15:36 neg | 0 | Neg | | 28.8 | 29.5 | 3800 | STEMI | 0 | 1 | 1 |
| 6__17:45 pos | 2 | Pos | 1.26 | 1227 | 33.3 | 7100 | STEMI | 0 | 1 | 1 |
| 7__15:25 neg | 0 | Neg | | 21.8 | 210.1 | 32700 | NSTEMI | 0 | 1 | 2 |
| 7__19:25 pos | 4 | Pos | 0.08 | 83.7 | 267.7 | 31900 | NSTEMI | 0 | 1 | 2 |
| 8__14:01 neg | 0 | Neg | | 20.5 | 66.2 | 2800 | STEMI | 1 | 1 | 2 |
| 8__15:28 pos | 1 | Pos | 0.54 | 585 | 69.2 | 1200 | STEMI | 1 | 1 | 2 |
| 9__18:17 neg | 0 | Neg | | 29.0 | 115.5 | <635 | STEMI | 1 | 1 | 1 |
| 9__20:38 pos | 2 | Pos | 0.05 | 62.5 | 134.7 | <635 | STEMI | 1 | 1 | 1 |
| 10__9:50 neg | 0 | Neg | | 20.2 | 19.4 | 840 | NSTEMI | 0 | 1 | 1 |
| 10__13:24 pos | 3 | Pos | 0.04 | 46.2 | 27.7 | <635 | NSTEMI | 0 | 1 | 1 |
| 11__3:45 neg | 0 | Neg | | 2.2 | 19.7 | 2100 | STEMI | 1 | 1 | 1 |
| 11__7:17 pos | 4 | Pos | 1.90 | 1420 | 34.8 | 6400 | STEMI | 1 | 1 | 1 |
| 12__14:39 neg | 0 | Neg | | 10.1 | 72.6 | <635 | NSTEMI | 0 | 1 | 1 |
| 12__17:58 pos | 3 | Pos | 0.20 | 168.9 | 62.9 | 4800 | NSTEMI | 0 | 1 | 1 |
| 13__13:00 | 0 | Neg | | 5.2 | 713.7 | <635 | | | | |
| 13__14:00 | 1 | Neg | | 5.0 | 656.9 | 2100 | | | | |
| 13__15:10 | 2 | Neg | | 4.7 | 691.7 | 380 | | | | |
| 14__11:45 | 0 | Neg | | 4.4 | 167.4 | 4100 | UAP | 0 | 1 | 1 |
| 14__12:15 | 1 | Neg | | 4.5 | 158.5 | 4500 | UAP | 0 | 1 | 1 |
| 14__13:15 | 2 | Neg | | 4.3 | 149.8 | 5200 | UAP | 0 | 1 | 1 |
| 14__14:15 | 3 | Neg | | 4.4 | 158.8 | 5900 | UAP | 0 | 1 | 1 |
| 15__13:00 | 0 | Neg | | 9.5 | 582.6 | 3500 | UAP | ? | 0 | 0 |
| 15__14:00 | 1 | Neg | | 8.7 | 618.1 | 1500 | UAP | ? | 0 | 0 |
| 15 15:00 | 2 | Neg | | 8.2 | 582.0 | 2300 | UAP | ? | 0 | 0 |
| 15__16:00 | 3 | Neg | | 9.7 | 582.0 | 2400 | UAP | ? | 0 | 0 |
| 16__12:45 | 0 | Neg | | 18.0 | 190.0 | 830 | UAP | 0 | 0 | 0 |
| 16__13:45 | 1 | Neg | | 22.5 | 224.7 | <635 | UAP | 0 | 0 | 0 |
| 16__14:45 | 2 | Neg | | 26.0 | 312.5 | <635 | UAP | 0 | 0 | 0 |
| 16__15:45 | 3 | Neg | | 25.4 | 338.7 | 1200 | UAP | 0 | 0 | 0 |
| 17__12:45 | 0 | Neg | | 15.5 | 294.9 | <635 | UAP | ? | 1 | 1 |
| 17__13:45 | 1 | Neg | | 20.6 | 380.4 | <635 | UAP | ? | 1 | 1 |
| 17__14:45 | 2 | Neg | | 21.6 | 387.4 | <635 | UAP | ? | 1 | 1 |
| 17__15:45 | 3 | Neg | | 24.0 | 387.9 | <635 | UAP | ? | 1 | 1 |
| 18__9:30 | 0 | Neg | | 8.2 | 461.6 | 5900 | UAP | 0 | 0 | 0 |
| 18__10:30 | 1 | Neg | | 11.0 | 533.8 | 10600 | UAP | 0 | 0 | 0 |
| 18__11:30 | 2 | Neg | | 11.1 | 553.4 | 3600 | UAP | 0 | 0 | 0 |
| 18__12:30 | 3 | Neg | | 10.5 | 568.1 | 10200 | UAP | 0 | 0 | 0 |
| 19__11:30 | 0 | Neg | | 0.0 | 711.3 | 10200 | UAP | 0 | 0 | 0 |
| 19__12:30 | 1 | Neg | | 0.2 | 784.4 | 8500 | UAP | 0 | 0 | 0 |
| 19__13:30 | 2 | Neg | | <LDL | 790.5 | 8100 | UAP | 0 | 0 | 0 |
| 19__14:30 | 3 | Neg | | <LDL | 766.7 | | UAP | 0 | 0 | 0 |
| 19__16:00 | 4 | Neg | | <LDL | 748.9 | 9700 | UAP | 0 | 0 | 0 |

Neg, negative;
Pos, positive;
PCTA, Percutaneous transluminal coronary angioplasty;
LDL, lower detection Limit,
NSTEMI, non-ST-elevated myocardial infarction,
STEMI, ST-elevated myocardial infarction;
UAP, unstable angina pectoris Diagnosis and the following interventions indicated that also patients in whom the initial levels of troponin T were negative had a cardiac disorder requiring treatment. In particular, at least in some of the patients later diagnosed as having suffered from unstable angina pectoris (UAP) a thrombus must have been present, although it was not detectable.

What is claimed is:

1. A method for distinguishing an acute cardiac event from a chronic cardiac disease in a patient presenting with symptoms of acute cardiac decompensation, the method comprising the steps of measuring in a sample from the patient, within 24 hours after occurrence of the symptoms, a level of NT-proANP or an isoform thereof having at least 80% sequence similarity, measuring in a sample from the patient, within 24 hours after occurrence of the symptoms, a level of NT-proBNP or an isoform thereof having at least 80% sequence similarity, and comparing the measured level of NT-proANP with the measured level of NT-proBNP as a means of distinguishing an acute cardiac event from a chronic cardiac disease, wherein a level of NT-proANP of more than 3000 pg/ml and a level of NT-proBNP of less than 1000 pg/ml indicates the presence of an acute cardiac event, and wherein a level of NT-proANP of more than 3000 pg/ml and a level of NT-proBNP of more than 3000 pg/ml and indicates the presence of a chronic cardiac disease.

2. The method according to claim 1 wherein measurements of NT-proANP and NT-proBNP are performed in parallel.

3. The method according to claim 1 wherein the sample is selected from the group consisting of blood, plasma, and serum.

4. The method according to claim 1 further comprising the step of measuring a level of NT-proANP in at least one additional sample.

5. The method according to claim 1 further comprising the step of measuring a level of NT-proBNP in at least one additional sample.

6. The method according to claim 1 wherein a time-course of NT-proANP and/or NT-proBNP is established.

7. The method according to claim 1 further comprising the step of expressing the measured levels of NT-proANP and NT-proBNP as a ratio.

8. The method according to claim 1 further comprising the step of measuring in a sample from the patient at least one biomarker selected from the group consisting of troponin T, creatine kinase (CK), creatine kinase muscle-brain (CK-MB), and myoglobin.

9. The method according to claim 1 further comprising the step of measuring a diagnostic indicator selected from the group consisting of left ventricular ejection fraction, echocardiogram, angina pectoris, electrocardiogram, parameters of thyroid or kidney function, arterial hypertension, thallium scintigram, angiography, and cardiac catheterization.

10. A method for recommending initiation of treatment of a patient for a cardiac disease, wherein the patient presents with symptoms of acute cardiac decompensation, the method comprising the steps of measuring in a sample from the patient, within 24 hours after occurrence of the symptoms, a level of NT-proANP or an isoform thereof having at least 80% sequence similarity, measuring in a sample from the patient, within 24 hours after occurrence of the symptoms, a level of NT-proBNP or an isoform thereof having at least 80% sequence similarity, comparing the measured level of NT-proANP with the measured level of NT-proBNP as a means of distinguishing an acute cardiac event from a chronic cardiac disease, wherein a level of NT-proANP of more than 3000 pg/ml and a level of NT-proBNP of less than 1000 pg/ml indicates the presence of an acute cardiac event, and wherein a level of NT-proANP of more than 3000 pg/ml and a level of NT-proBNP of more than 3000 pg/ml and indicates the presence of a chronic cardiac disease, optionally initiating an examination of the patient by a cardiologist, and recommending the initiation of treatment if the comparison step indicates the presence of a cardiac disease.

* * * * *